(12) United States Patent
Segawa

(10) Patent No.: US 8,128,560 B2
(45) Date of Patent: Mar. 6, 2012

(54) POWER-SUPPLY STARTER APPARATUS FOR CAPSULE-TYPE MEDICAL DEVICE, START METHOD OF CAPSULE-TYPE MEDICAL DEVICE, AND STOP METHOD OF POWER SUPPLY FOR CAPSULE-TYPE MEDICAL DEVICE

(75) Inventor: Hidetake Segawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1461 days.

(21) Appl. No.: 11/590,141

(22) Filed: Oct. 31, 2006

(65) Prior Publication Data

US 2008/0103372 A1    May 1, 2008

(51) Int. Cl.
*A61B 5/07* (2006.01)

(52) U.S. Cl. ............................. 600/302; 600/7; 600/15

(58) Field of Classification Search .................. 600/300, 600/302, 7, 15; 206/439, 363, 461–467
See application file for complete search history.

(56) References Cited

U.S. PATENT DOCUMENTS

| 7,766,167 | B2 * | 8/2010 | Segawa | 206/439 |
| 7,770,725 | B2 * | 8/2010 | Segawa | 206/363 |

FOREIGN PATENT DOCUMENTS

| JP | 2003-210395 | | 7/2003 |
| JP | 2006-094933 | | 4/2006 |
| JP | 2006-223473 | * | 8/2006 |
| WO | WO 01/35813 A1 | | 5/2001 |

* cited by examiner

*Primary Examiner* — Patricia Mallari
*Assistant Examiner* — Michael D'Angelo
(74) *Attorney, Agent, or Firm* — Scully, Scott, Murphy & Presser, P.C.

(57) ABSTRACT

A power-supply starter apparatus for a capsule-type medical device that includes a container case internally retaining a capsule-type medical device having at least a intra-subject information acquiring unit and a power switch for switching power supply to each unit including the intra-subject information acquiring unit, and a starter that has a magnetic body and controls switching of the power supply by applying a magnetic field originating from the magnetic body to the power switch of the capsule-type medical device inside the container case, wherein the container case has an insertion/removal unit in which a space is formed where the magnetic body can be brought closer to the power switch and the starter is inserted/removed, and the insertion/removal unit and starter have a restriction unit for restricting rotation around an axis in an insertion/removal direction of the starter into/from the insertion/removal unit so that switching of the power supply is controlled only by an insertion/removal operation of the starter is provided.

7 Claims, 22 Drawing Sheets

POWER-SUPPLY STARTER APPARATUS FOR CAPSULE-TYPE MEDICAL DEVICE, START METHOD OF CAPSULE-TYPE MEDICAL DEVICE, AND STOP METHOD OF POWER SUPPLY FOR CAPSULE-TYPE MEDICAL DEVICE

BACKGROUND OF THE INVENTION

1. Field of the Invention

The present invention relates to a power-supply starter apparatus for a capsule-type medical device for starting power supply for each function executing unit in a capsule-type medical device such as a swallowable capsule endoscope which is inserted into a subject to acquire intra-subject information such as image information of an interior of the subject, a start method of the capsule-type medical device, and a stop method of power supply for the capsule-type medical device.

2. Description of the Related Art

In recent years, a capsule endoscope equipped with an image pickup function and a radio function has appeared in a field of endoscope. The capsule endoscope is configured to move inside organs such as the stomach and small intestine (inside body cavities) following peristaltic movements thereof during an observation period after being swallowed by a patient, which is a subject, for observation (examination) until naturally discharged from a living body (human body) of the subject, and to successively pick up images using the image pickup function.

Image data captured by the capsule endoscope inside body cavities during the observation period while the capsule endoscope moves inside the organs is sequentially transmitted by the radio function such as radio communication to an external device provided outside the subject and stored in a memory provided inside the external device. By carrying the external device with the radio function and memory function, the subject can move freely without inconvenience during an observation period, i.e., after swallowing the capsule endoscope until discharging the same. After the observation, a doctor or a nurse can make a diagnosis by displaying body-cavity images on a display unit such as a display based on the image data accumulated in the memory of the external device.

One type of the above capsule endoscopes is described in, for example, WO 01/35813, which proposes a configuration of a capsule endoscope having internally a reed switch turned on/off by an external magnetic field to control driving of a capsule endoscope and contained in a package including a permanent magnet supplying the external magnetic field. The reed switch provided in the capsule endoscope maintains an off state in an environment in which a magnetic field of a certain intensity or more is provided and is turned on when the external field intensity decreases. Thus, the capsule endoscope is not driven while contained in a package. Then, when the capsule endoscope is taken out from the package to be swallowed, driving of the capsule endoscope starts since an influence of magnetic force being exerted on the capsule endoscope disappears as the capsule endoscope moves away from the permanent magnet. By providing such a configuration, driving of the capsule endoscope can be prevented when contained in a package, and after being taken out of the package, images are taken by the image pickup function of the capsule endoscope, with image signals being transmitted by the radio function.

However, such a device has a problem that, since it takes some time after the capsule endoscope is taken out of the package until introduced into the subject, each function of the capsule endoscope, for example, the image pickup function and the radio function, starts driving in the meantime and the image pickup function performs an image pickup operation of images and, further, the radio function performs a radio transmission operation of picked-up images and thus power stored in the capsule endoscope is wasted.

On the other hand, Japanese Patent Application Laid-Open No. 2006-223473 discloses a configuration in which a starter is inserted into an inner lid unit and rotated up to 90° in a circumferential direction of the capsule endoscope to turn on the capsule endoscope.

However, such a configuration has a problem that, if the starter is rotated fast, the reed switch may not be turned on/off correctly and thus the capsule endoscope cannot be turned on reliably.

SUMMARY OF THE INVENTION

An object of the present invention is to provide a power-supply starter apparatus for a capsule-type medical device that can reliably turn on and turn off a capsule-type medical device at any time, a start method of the capsule-type medical device, and a stop method of power supply for the capsule-type medical device.

A power-supply starter apparatus for a capsule-type medical device according to one aspect of the present invention includes a container case internally retaining a capsule-type medical device having at least a intra-subject information acquiring unit and a power switch which switches power supply to each unit including the intra-subject information acquiring unit, and a starter having a magnetic body to control switching of the power supply by applying a magnetic field generated by the magnetic body to the power switch of the capsule-type medical device inside the container case, wherein the container case has an insertion/removal unit in which a space is formed where the magnetic body can be brought closer to the power switch and the starter is inserted and removed, and the insertion/removal unit and the starter have a restriction unit for restricting rotation of the starter around an axis in an insertion/removal direction into/from the insertion/removal unit so that switching of the power supply is controlled only by an insertion/removal operation of the starter.

Further, the power-supply starter apparatus may further include a latch circuit for providing toggle switching output by frequency dividing a switching signal of the power switch, wherein the switching of power supply to each unit including the intra-subject information acquiring unit may be controlled by the toggle switching output from the latch circuit.

Further, in the power-supply starter apparatus, the restriction unit may include guide grooves provided in the insertion/removal unit for guiding the starter in the insertion/removal direction and projections provided on the starter to engage with the guide grooves.

Further, in the power-supply starter apparatus for the capsule-type medical device, the power switch may be a reed switch and may be arranged so that a direction perpendicular to an axis in a longitudinal direction of the capsule-type medical device is a longitudinal direction of the reed switch, the starter may be inserted and removed in the longitudinal direction of the capsule-type medical device, the magnetic body may be arranged so that a magnetic field is applied to the reed switch from the longitudinal direction of the reed switch, and the guide grooves may be arranged at intervals of less than 90° around the axis in the insertion/removal direction.

Further, in the power-supply starter apparatus for the capsule-type medical device, there may be five or more guide grooves provided at equiangular intervals.

Further, in the power-supply starter apparatus for the capsule-type medical device, the restriction unit may restrict the rotation based on an inner cross sectional shape of the insertion/removal unit perpendicular to the insertion/removal direction and an outer cross sectional shape of the starter perpendicular to the insertion/removal direction.

Further, in the power-supply starter apparatus for the capsule-type medical device, the restriction unit may position the insertion/removal unit and the starter in a rotational direction, and the capsule-type medical device may be arranged inside the container case in advance so that a magnetic detection direction of the power switch of the capsule-type medical device and a direction of magnetism generated by the magnetic body of the starter match.

Further, a power-supply starter apparatus for a capsule-type medical device according to another aspect of the present invention includes a container case internally retaining a capsule-type medical device, the capsule-type medical device including at least a power source, an intra-subject information acquiring unit, and a reed switch, the capsule-type medical device including a latch circuit which provides a toggle switching output by frequency dividing a switching signal from the reed switch, and the capsule-type medical device switching power supply from the power source to each unit including the intra-subject information acquiring unit by the toggle switching output from the latch circuit, and a starter having a magnetic body to control the switching of the power supply by applying a magnetic field generated by the magnetic body to the reed switch of the capsule-type medical device inside the container case, wherein the container case has an insertion/removal unit in which a space is formed where the magnetic body can be brought closer to the reed switch and the starter is inserted/removed, the reed switch is arranged so that a longitudinal direction of the capsule-type medical device coincides with a longitudinal direction of the reed switch, the starter is inserted and removed in the longitudinal direction of the capsule-type medical device with a longitudinal axis of the capsule-type medical device set as a center, and the magnetic body is arranged so that a magnetic field is applied to the reed switch in the longitudinal direction of the capsule-type medical device.

Further, in the power-supply starter apparatus for the capsule-type medical device the magnetic body may be a magnet.

Further, in the power-supply starter apparatus for the capsule-type medical device, the capsule-type medical device may be a capsule-type medical device having an imaging unit as the intra-subject information acquiring unit.

Further, a start method of a capsule-type medical device according to still another aspect of the present invention includes the steps of applying a magnetic field to a capsule-type medical device, confirming starting of the capsule-type medical device, and removing the magnetic field applied to the capsule-type medical device.

Further, in the start method of the capsule-type medical device, the step of applying the magnetic field may include a step of bringing a starter having a magnetic body closer to the capsule-type medical device.

Further, in the start method of the capsule-type medical device, the step of bringing the starter closer may include a step of bringing the starter closer in a longitudinal direction of the capsule-type medical device.

Further, in the start method of the capsule-type medical device, the step of confirming the starting may include a step of confirming that an illuminating member of the capsule-type medical device is lighting.

Further, the start method may further include the steps of, when the starting of the capsule-type medical device cannot be confirmed in the step of confirming the starting, removing the magnetic field applied to the capsule-type medical device, applying a magnetic field to the capsule-type medical device by changing an angle of the magnetic field, confirming the starting of the capsule-type medical device, and removing the magnetic field applied to the capsule-type medical device.

Further, a stop method of power supply for a capsule-type medical device according to still another aspect of the present invention includes the steps of applying a magnetic field to the capsule-type medical device, confirming a stop of the power supply for the capsule-type medical device, and removing the magnetic field applied to the capsule-type medical device.

Further, in the stop method of the power supply for the capsule-type medical device, the step of applying the magnetic field may include a step of bringing a starter having a magnetic body closer to the capsule-type medical device.

Further, the stop method of the power supply for the capsule-type medical device, the step of bringing the starter closer may include a step of bringing the starter closer in a longitudinal direction of the capsule-type medical device.

Further, the stop method of the power supply for the capsule-type medical device, the step of confirming the stop may include a step of confirming that an illuminating member of the capsule-type medical device has been put out.

Further, the stop method may further include the steps of, when the stop of the power supply for the capsule-type medical device cannot be confirmed in the step of confirming the stop, removing the magnetic field applied to the capsule-type medical device, applying a magnetic field to the capsule-type medical device by changing an angle of the magnetic field, confirming the stop of the power supply for the capsule-type medical device, and removing the magnetic field applied to the capsule-type medical device.

What has been described above and other objects, features, advantages, and technical and industrial significance of the present invention will be further understood by reading detailed descriptions of the present invention below with reference to attached drawings.

DETAILED DESCRIPTION OF THE PREFERRED EMBODIMENTS

Embodiments of a power-supply starter apparatus for a capsule-type medical device according to the present invention including a power-supply starter for a capsule-type medical device and a container case, a start method of a capsule-type medical device, and a stop method of power supply for the capsule-type medical device will be described below in detail with reference to drawings. However, the present invention is not limited to these embodiments and may be carried out in various forms and variations without departing from the spirit of the present invention.

First Embodiment

Figure 1:
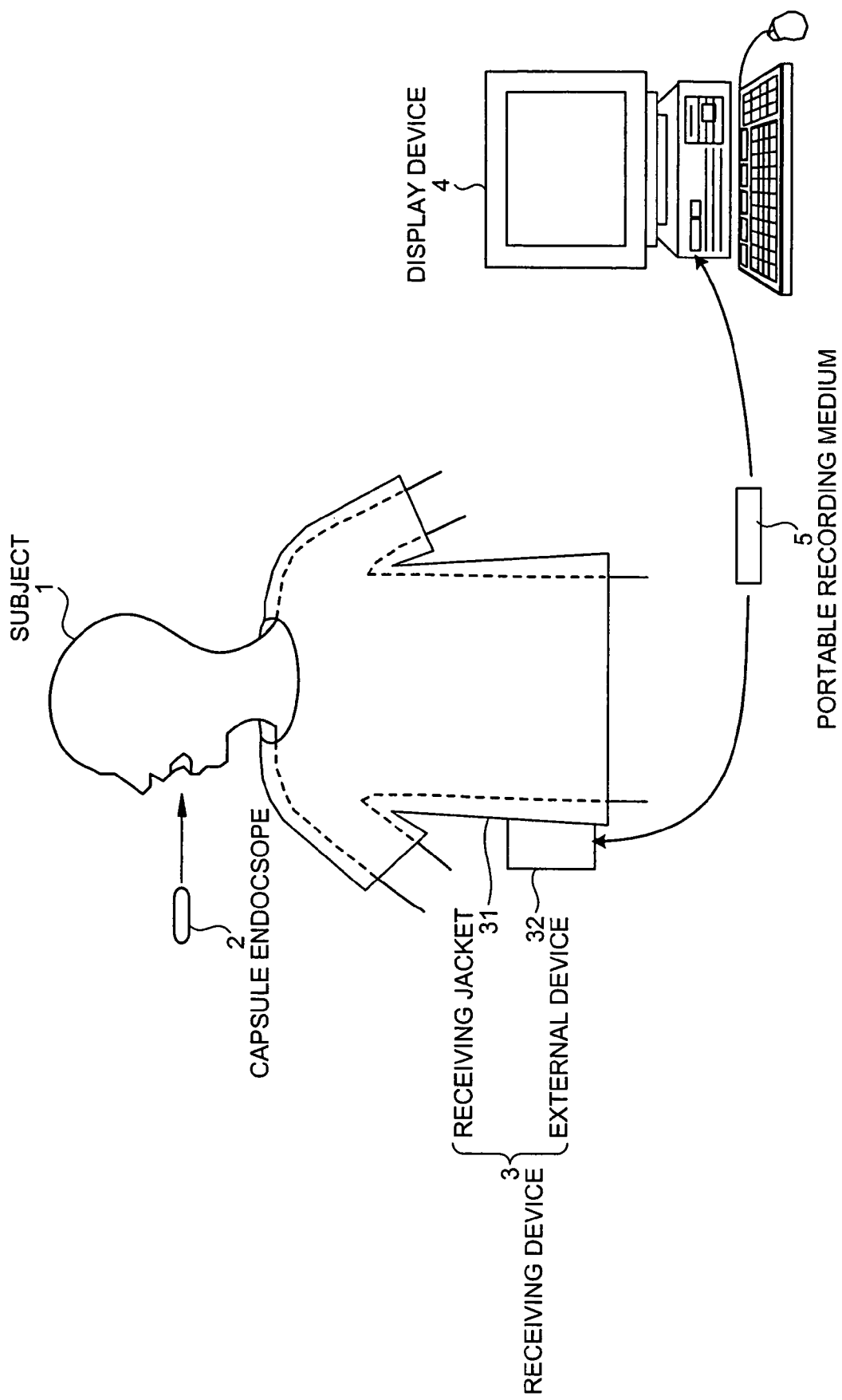
FIG. 1 is a system conceptual diagram showing a concept of a radio intra-subject information acquiring system including a capsule-type medical device whose power supply has been started by a starter for a capsule-type medical device according to the present invention.

FIG. 1 is a system conceptual diagram showing a concept of a radio intra-subject information acquiring system in which a capsule-type medical device for which a power-supply starter apparatus for a capsule-type medical device according to the present invention is intended is used. In FIG. 1, the radio intra-subject information acquiring system includes a swallowable capsule-type medical device 2 as a radio intra-subject information acquiring device introduced into body cavities of a subject 1 and a receiving device 3 that is arranged outside the subject 1 as an external device and communicates various kinds of information with the capsule-type medical device 2 by radio. The radio intra-subject information acquiring system also includes a display device 4 for displaying images based on data received by the receiving device 3 and a portable recording medium 5 for data delivery between the receiving device 3 and the display device 4.

Figure 2:
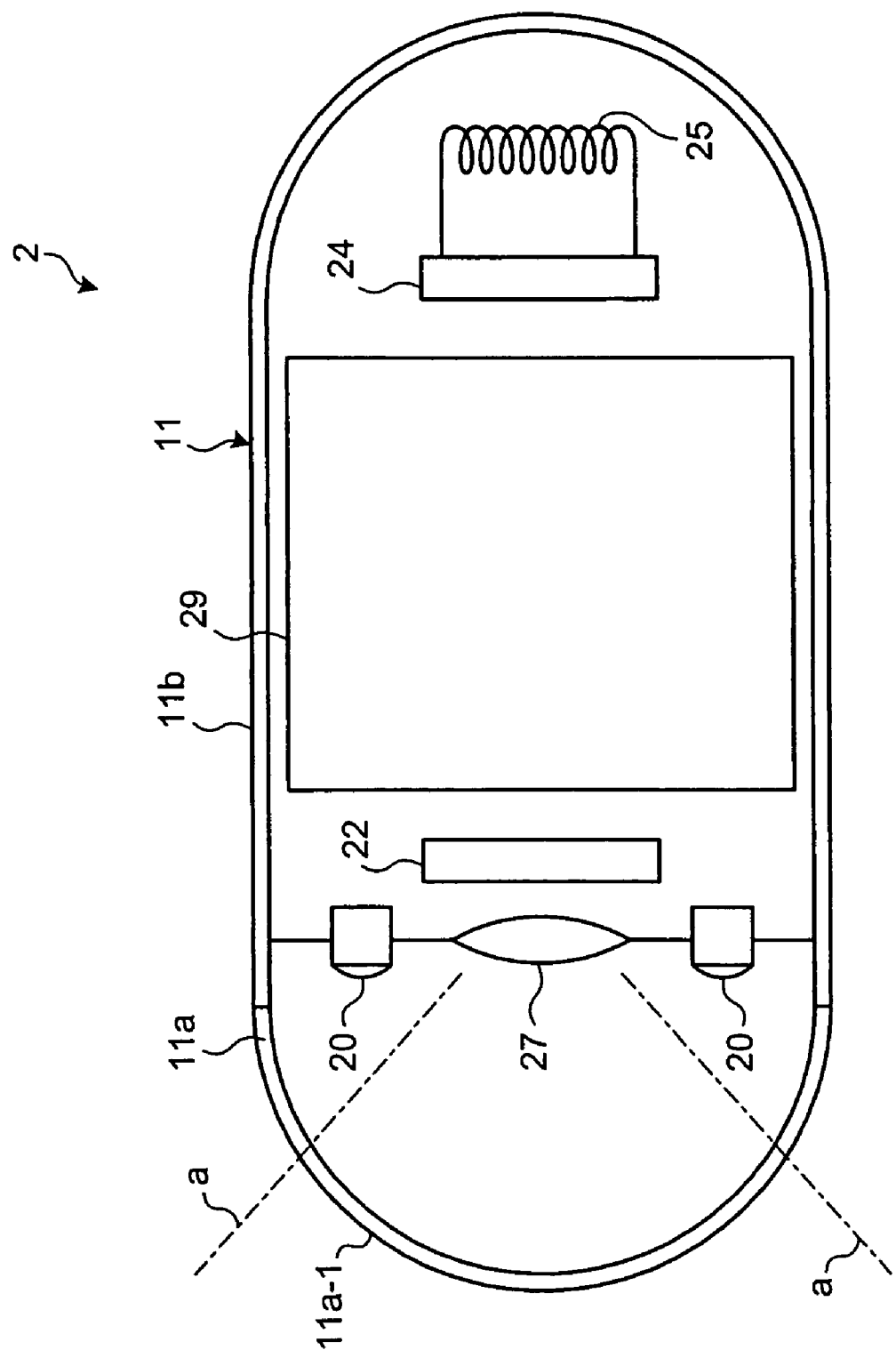
FIG. 2 is a longitudinal sectional view showing an outline configuration of the capsule-type medical device shown in FIG. 1.

The capsule-type medical device 2 includes, as shown in the sectional view of FIG. 2, a hermetic container 11, which is an exterior container case, a plurality of light emitting devices 20 such as LEDs that are inside the hermetic container 11 and emit an illumination light for illuminating, for example, examined regions inside body cavities, a solid-state imaging device 22 (hereinafter exemplarily referred to as "CCD 22") such as a CCD and a CMOS that picks up images of the examined regions by receiving a reflected light of the illumination light, an imaging lens 27 that focuses an image of an object in the CCD 22, an RF transmitting unit 24 that modulates image information obtained by the CCD 22 into an RF signal and transmits the RF signal, a transmitting antenna unit 25 that transmits radio waves of the RF signal, a battery 29, and the like.

The present capsule-type medical device can be said to have an imaging unit as an intra-subject information acquiring unit that acquires image information.

The hermetic container 11 has such a size that a person can swallow the same, and forms an exterior container case that includes a substantially hemispherical distal-end cover 11a and a cylindrical trunk cover 11b that elastically fit with each other so as to provide a liquid-tight sealing. The distal-end cover 11a has an approximately hemispherical dome shape and a circular opening on a rear side of the dome. The distal-end cover 11a is formed of a transparent member or a member having transparency such as cycloolefin polymers or polycarbonate that is preferable to ensure optical performance and strength, and has on its surface a mirror finish unit 11a-1 described later to which mirror finish treatment is applied, allowing an illumination light from the light emitting devices 20 to transmit out of the hermetic container 11 and also a reflected light of the illumination light from a subject to transmit into the inner part. The mirror finish unit 11a-1 is formed in a fixed mirror finish range (range indicated by a dashed dotted line a-a in FIG. 2) determined by an imaging range of the solid-state imaging device 22 and the like.

The trunk cover 11b is a member positioned at a rear end of the distal-end cover 11a to cover the above-described components. The trunk cover 11b is integrally formed from a cylindrical trunk and an approximately hemispherical dome-shaped rear end part and has a circular opening on a front side of the trunk. The trunk cover 11b is formed of, for example, polysulfone that is preferable to ensure strength, and contains an illuminating unit, an imaging unit, and the battery 29 described later in the trunk and a radio transmitting unit in the rear end part.

Figure 3:
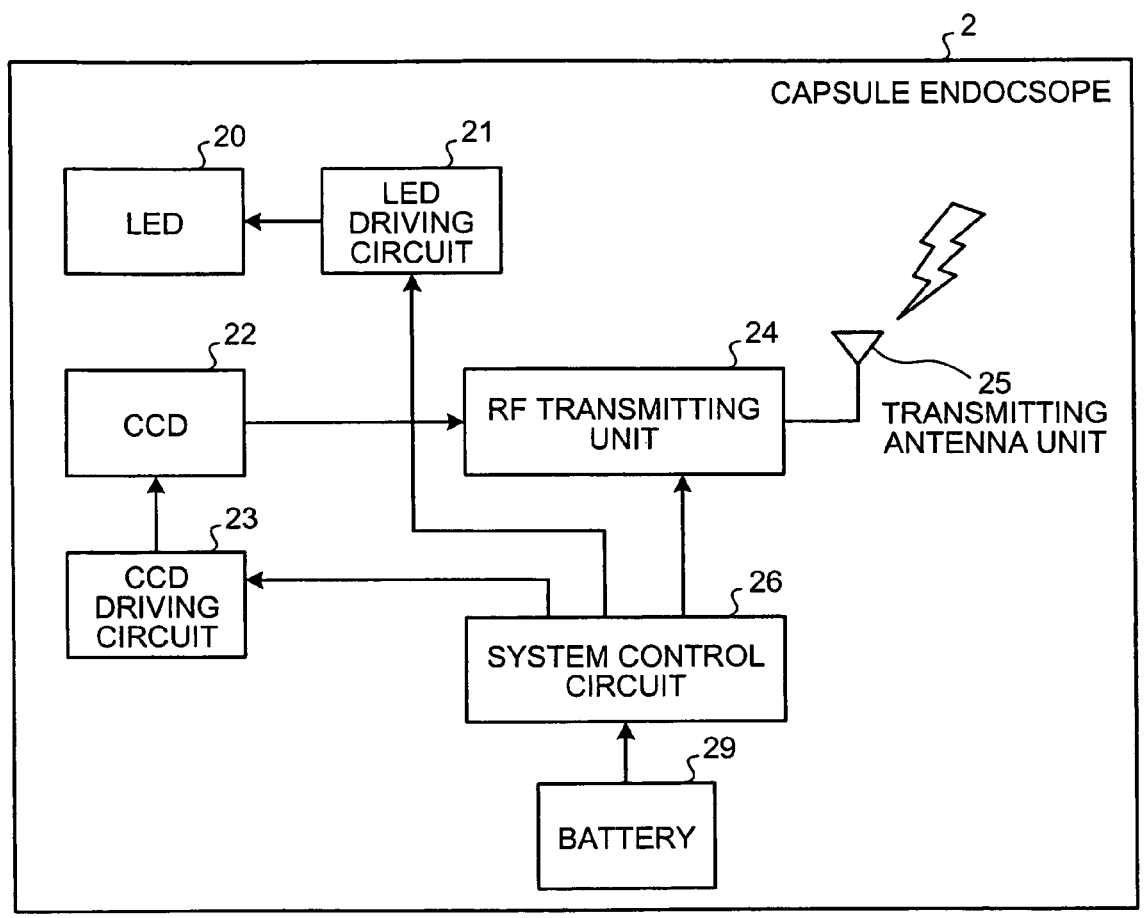
FIG. 3 is a block diagram showing an internal configuration of the capsule-type medical device shown in FIG. 2.

The capsule-type medical device 2 includes inside the hermetic container 11, as shown in the block diagram of FIG. 3, LEDs 20 as the illumination units, an LED driving circuit 21 for controlling a driving state of the LEDs 20, the CCD 22 as the imaging unit for picking up images (intra-subject information), which are a reflected light from an area illuminated by the LEDs 20, inside body cavities via the imaging lens 27, a CCD driving circuit 23 for controlling the driving state of the CCD 22, the RF transmitting unit 24 as the radio transmitting unit, and the transmitting antenna unit 25.

Further, by including a system control circuit 26 that controls operations of these LED driving circuit 21, CCD driving circuit 23, and RF transmitting unit 24, the capsule-type medical device 2 operates to acquire image data of regions to be examined illuminated by the LEDs 20 while the capsule-type medical device 2 is inside the subject 1. The acquired image data is further converted into an RF signal by the RF transmitting unit 24 and transmitted out of the subject 1 via the transmitting antenna unit 25. Further, the capsule-type medical device 2 has the battery 29 to supply power to the system control circuit 26 and the system control circuit 26 has a function to distribute driving power supplied from the battery 29 to other components (function executing unit).

The system control circuit 26 includes, for example, a switching device having a switching function and connected between each component and the battery 29, and a latch circuit. The latch circuit turns on the switching device when an external magnetic field is applied and maintains thereafter an on state to supply driving power from the battery 29 to each component inside the capsule-type medical device 2. In the first embodiment, the imaging unit having an imaging function, the illuminating unit having an illumination function, and the radio transmitting unit having a radio function provided in the capsule-type medical device 2 are generically called the function executing unit that executes predetermined functions. More specifically, excluding the system control circuit 26, every component is a function executing unit that executes a predetermined function set in advance.

The receiving device 3 has a function as a radio transmitting unit that receives image data inside body cavities transmitted from the capsule-type medical device 2 by radio, as can be seen from FIG. 1. The receiving device 3 includes a receiving jacket 31 which the subject 1 wears and has a plurality of receiving antennas (not shown) and an external device 32 for performing signal processing or the like of received radio signals. Alternatively, the receiving jacket 31 may be eliminated and the plurality of receiving antennas may be attached to a body surface.

The display device 4 is used to display images inside body cavities picked up by the capsule-type medical device 2 and has a configuration like a workstation that displays images based on data obtained from the portable recording medium 5. More specifically, the display device 4 may be configured to directly display images on a CRT display or a LCD, for example, or to output images to another medium like a printer.

The portable recording medium 5 can be connected to the external device 32 and the display device 4 and has a structure to be inserted into the external device 32 and the display device 4 so as to output or record information when connected. In the first embodiment, while the capsule-type medical device 2 moves inside body cavities of the subject 1, the portable recording medium 5 is inserted in the external device 32 to record data transmitted from the capsule-type medical device 2. After the capsule-type medical device 2 is discharged from the subject 1, that is, after image pick-up inside the subject 1 is completed, the portable recording medium 5 is removed from the external device 32 and inserted into the display device 4 so that data recorded in the portable recording medium 5 is read. For example, the portable recording medium 5 can be formed of Compact Flash (registered trademark) memory or the like so that the data input/output between the external device 32 and display device 4 is performed indirectly via the portable recording medium 5. Thus, in contrast to a case in which the external device 32 and the display device 4 are directly connected by a cable, the subject 1 can move freely during image pick-up inside body cavities.

Figure 4:
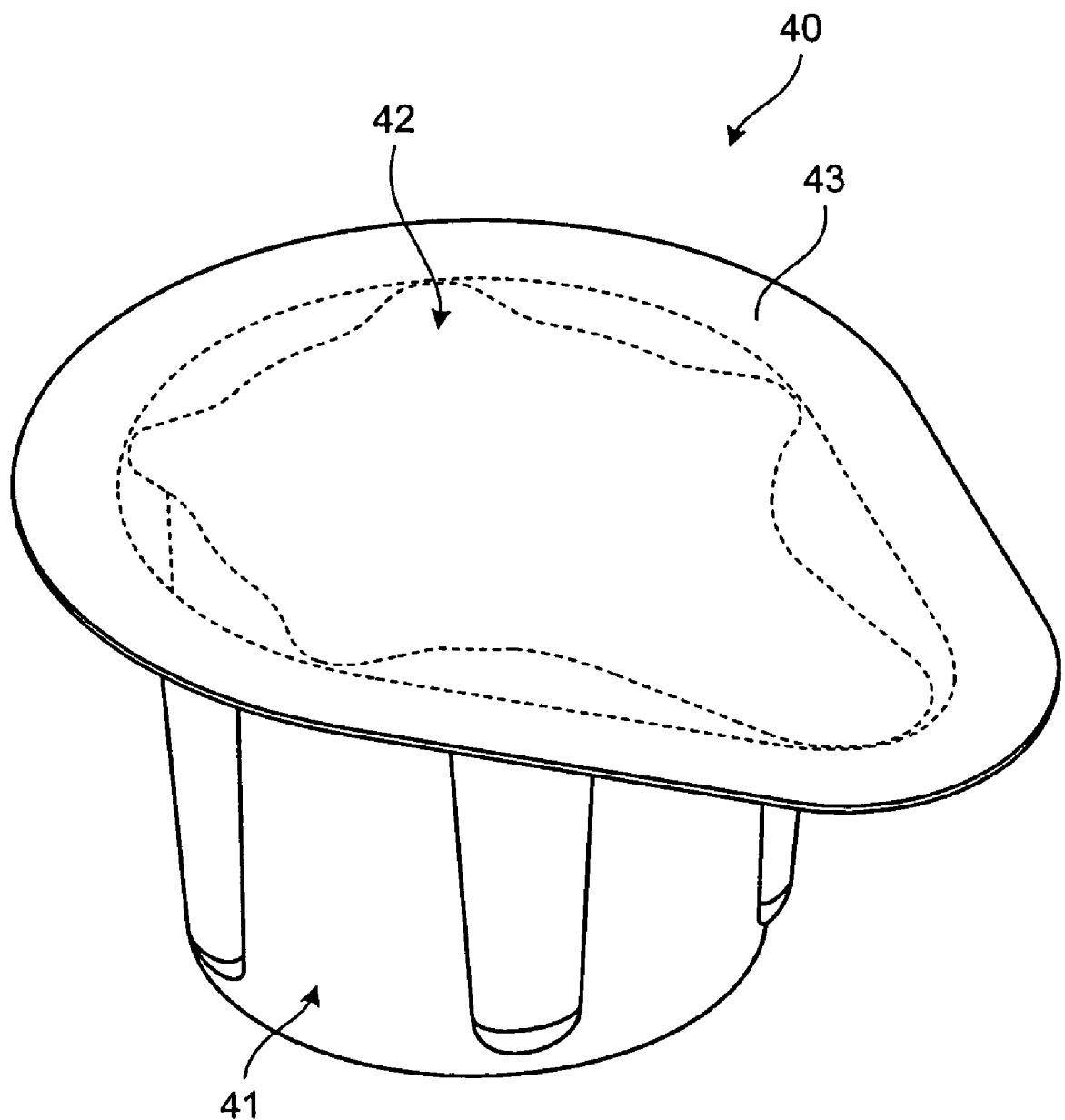
FIG. 4 is a perspective view of the configuration of a container case in which the capsule-type medical device is contained.
Figure 5:
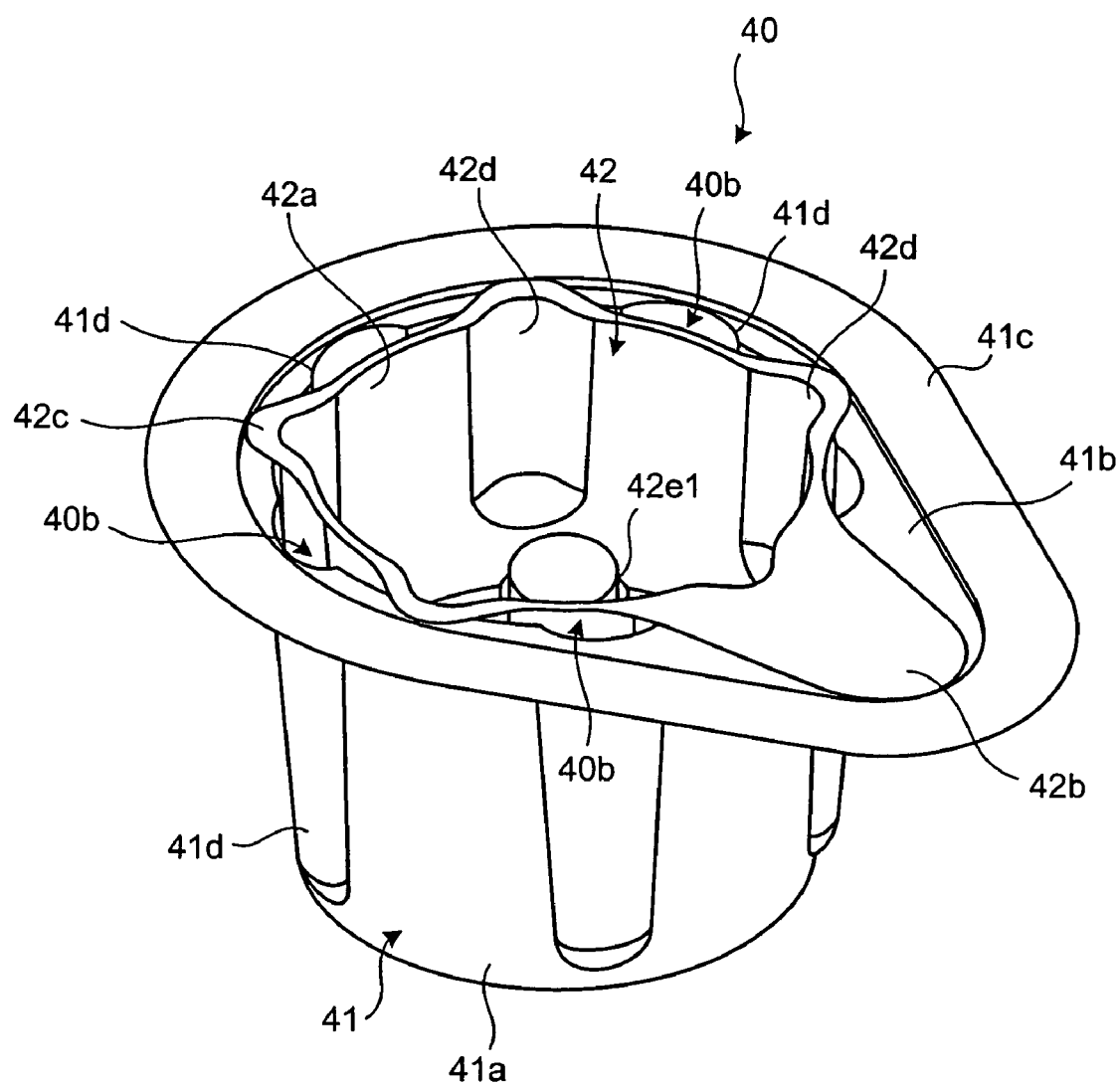
FIG. 5 is a perspective view of the container case after a sterilized sheet shown in FIG. 4 is removed.
Figure 6:
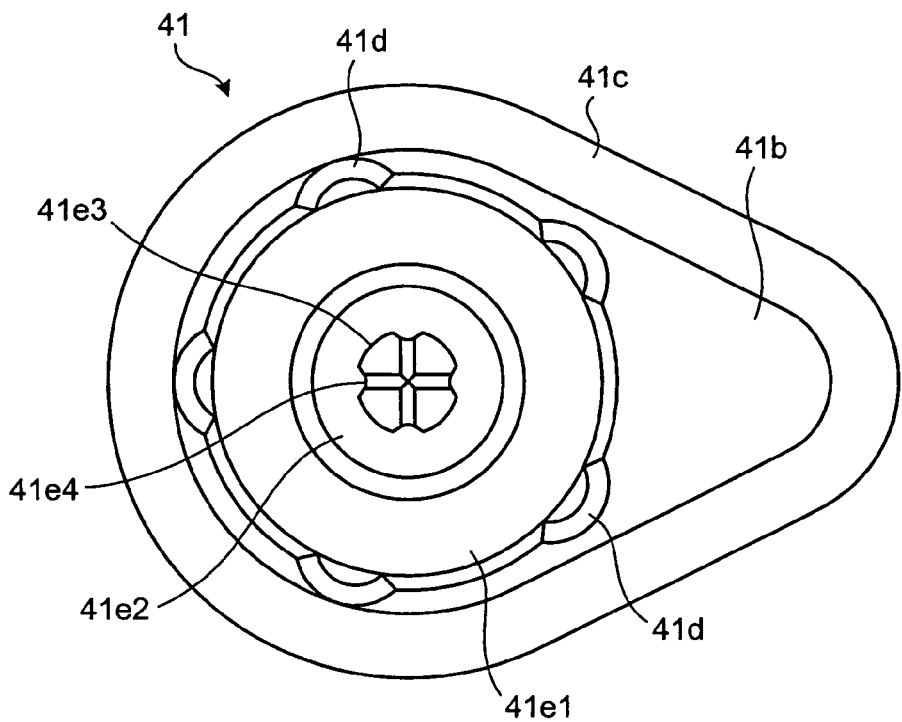
FIG. 6 is a plan view of a blister pack shown in FIG. 5.
Figure 7:
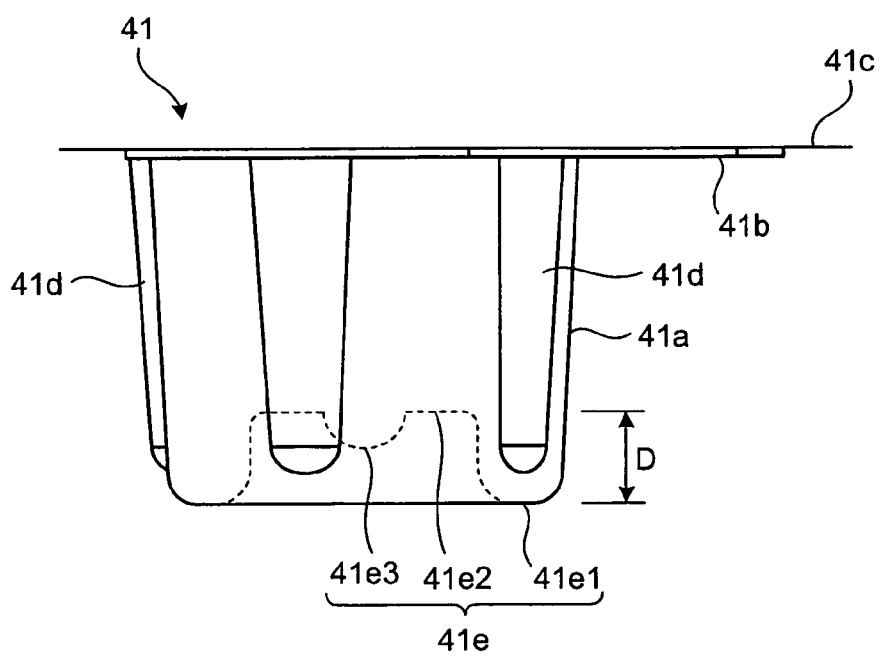
FIG. 7 is a side view of the blister pack shown in FIG. 5.
Figure 8:
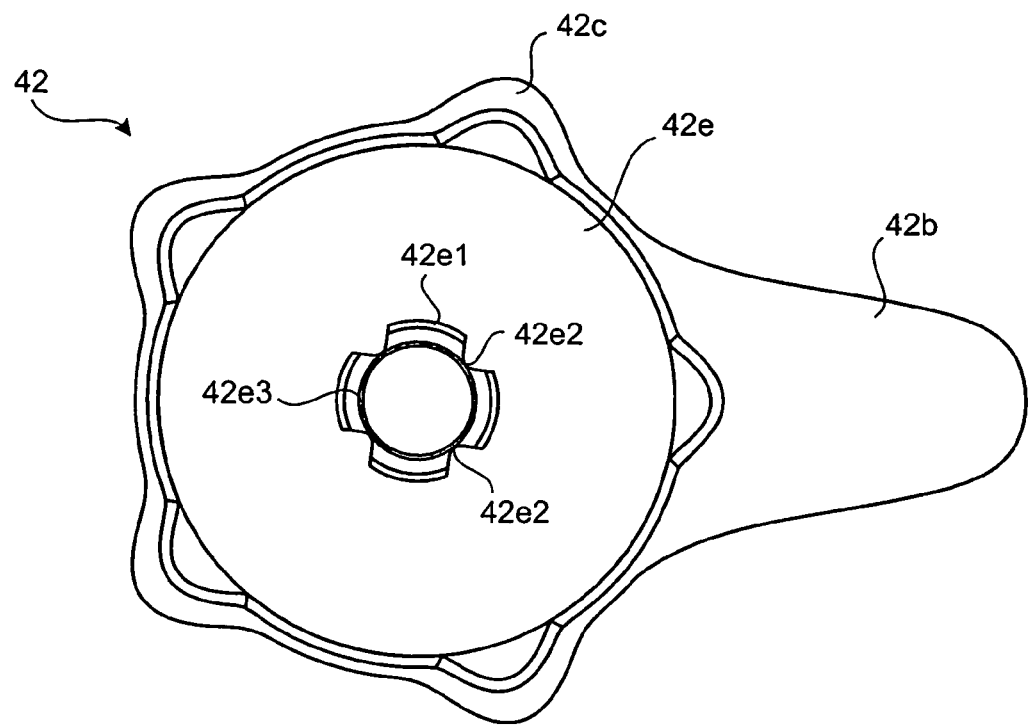
FIG. 8 is a plan view of an inner lid unit shown in FIG. 5.
Figure 9:
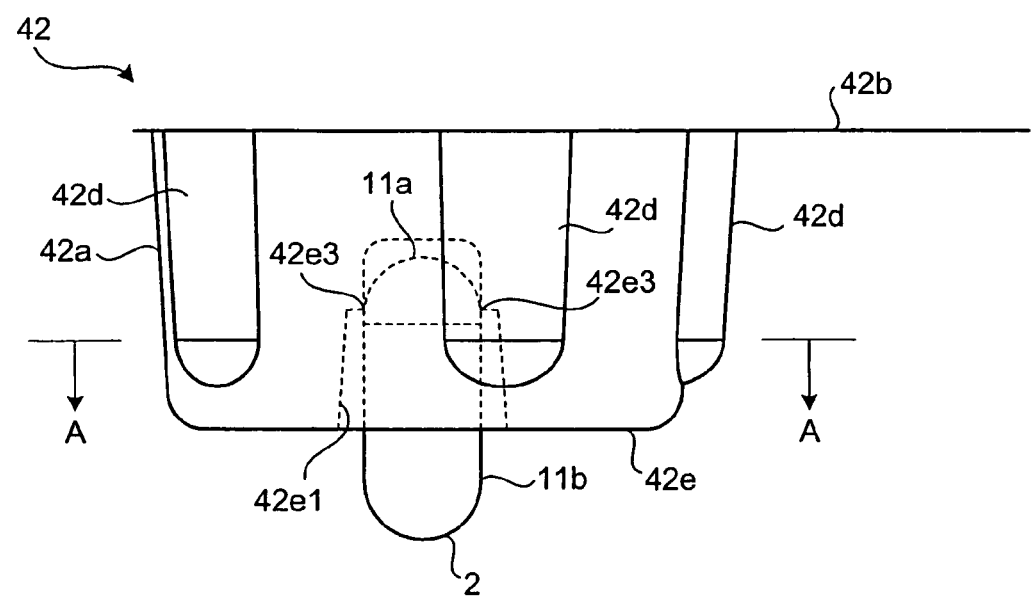
FIG. 9 is a side view of the inner lid unit shown in FIG. 5.
Figure 10:
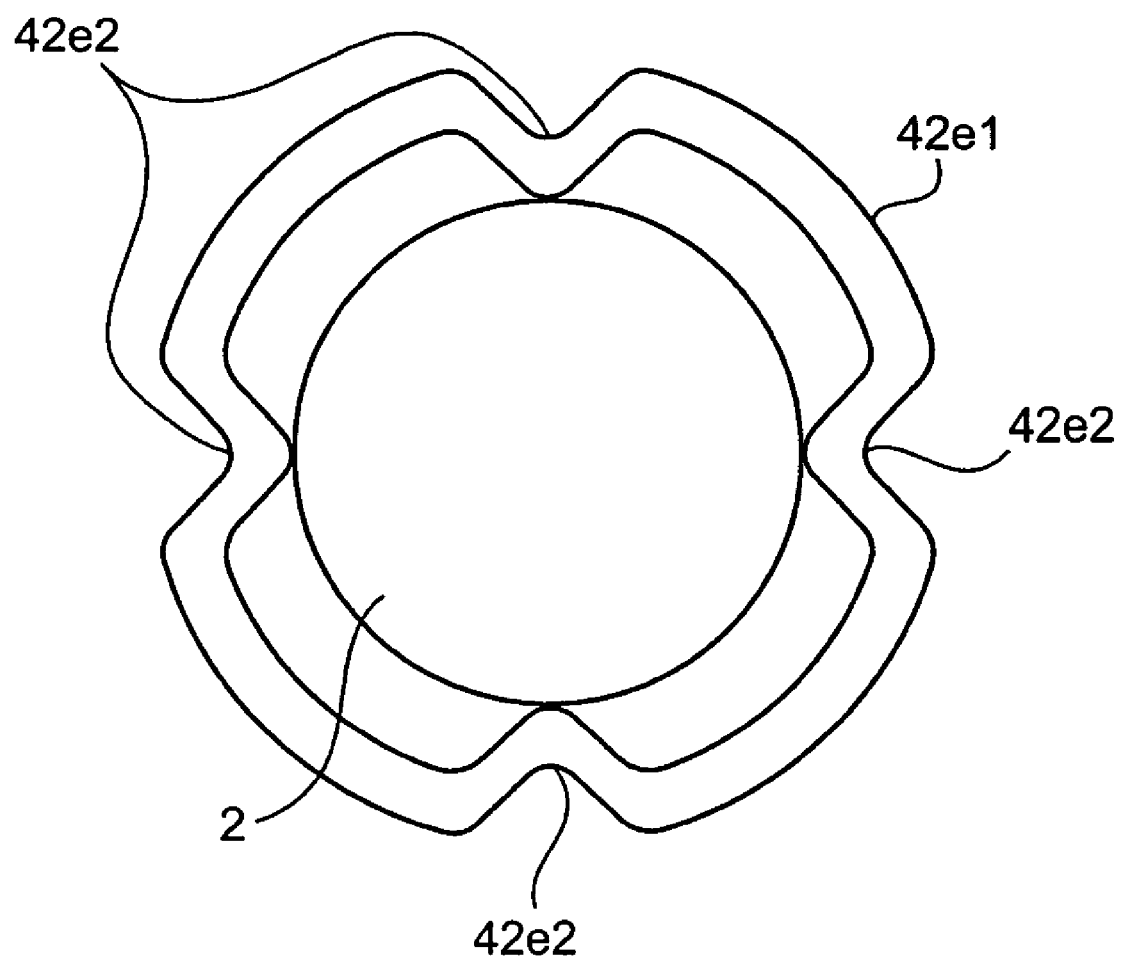
FIG. 10 is an A-A line sectional view of an enlarged hole shown in FIG. 9.
Figure 11:
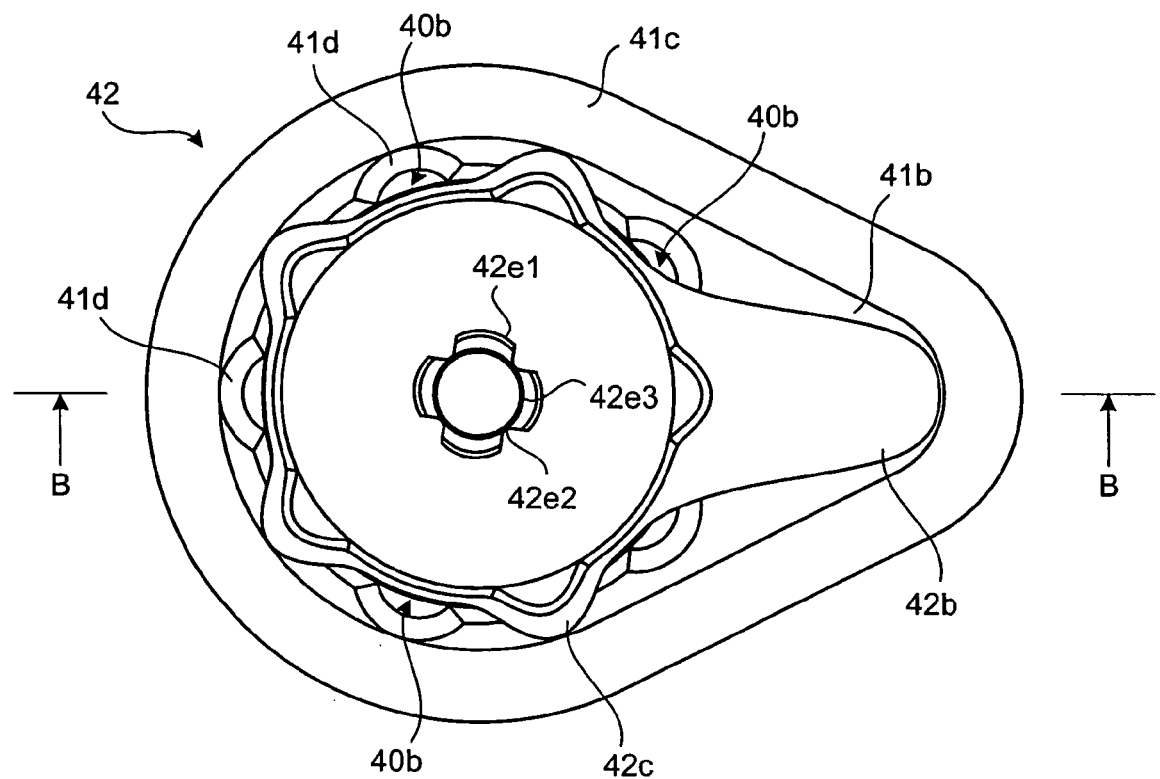
FIG. 11 is a plan view of the container case shown in FIG. 5.
Figure 12:
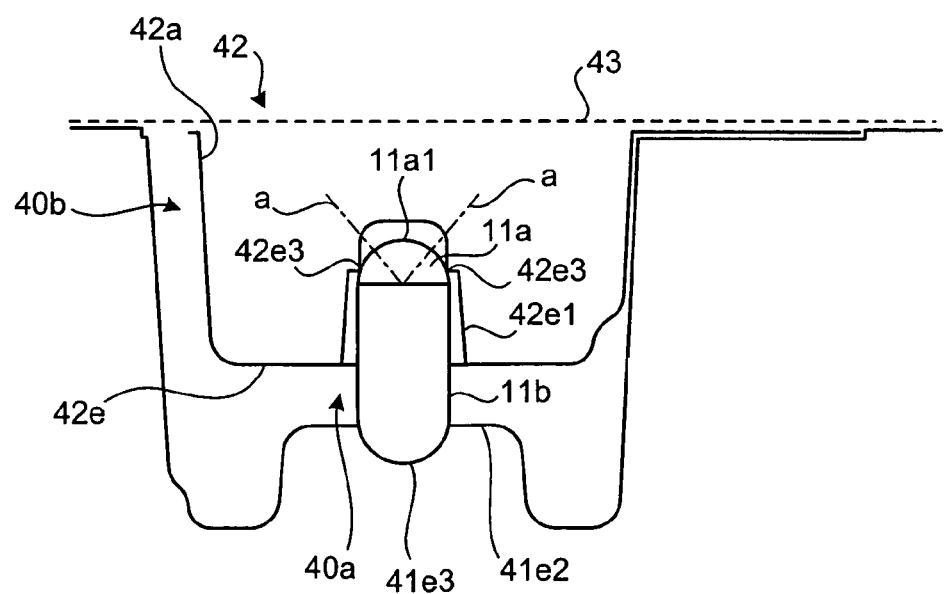
FIG. 12 is a B-B line sectional view of the container case shown in FIG. 11.

The capsule-type medical device having the function executing unit must be sterilized and kept in a sterilized state until used for the subject. In the first embodiment, the capsule-type medical device 2 is contained in a sterilizable container case. With reference to FIGS. 4 to 12, the container case according to the first embodiment will be described below. FIG. 4 is a perspective view showing the configuration of a container case containing a capsule-type medical device, FIG. 5 is a perspective view of an example of the container case shown in FIG. 4 after removing a sterilized sheet, FIG. 6 is a plan view of the container case shown in FIG. 5, FIG. 7 is a side view of the container case, FIG. 8 is a plan view of an inner lid unit shown in FIG. 5, FIG. 9 is a side view showing a side of the inner lid unit, FIG. 10 is a sectional view showing an enlarged A-A cross section of a hole shown in FIG. 9, FIG. 11 is a plan view of the container case shown in FIG. 5, and FIG. 12 is a sectional view showing a B-B cross section shown in FIG. 11.

In FIGS. 4 and 5, a container case 40 includes a blister pack 41 which forms an external containing unit in which the capsule-type medical device 2 can be housed, an inner lid unit 42 which is arranged inside the blister pack 41 and forms an inner containing unit so that the capsule-type medical device 2 is held between the blister pack 41 and the inner lid unit 42, and a sterilized sheet 43 which is provided on an upper surface of the blister pack 41 to close an opening of the blister pack 41. The blister pack 41 and the inner lid unit 42 are formed of a material such as polypropylene and shaped by a molding process such as vacuum forming.

The blister pack 41 includes, as shown in FIGS. 6 and 7, a bottomed cylindrical portion 41a, a tongue-shaped handle portion 41b provided in a part of an upper hem of an opening of the cylindrical portion 41a, an edge portion 41c provided around the upper hem of the opening of the cylindrical portion 41a and an outer circumference of the handle portion 41b, and a plurality of substantially half-column-shaped projections 41d bulging in an outward direction from the cylindrical portion 41a.

The cylindrical portion 41a has a bottom 41e which includes an outer bottom 41e1 provided on an outer circumferential side of the cylindrical portion 41a and an inner bottom 41e2 provided in an approximately central part of the outer bottom 41e1. The inner bottom 41e2 is formed in a disk shape having a predetermined radius, and the outer bottom 41e1 consists of a bottom projecting outwardly (i.e., in a direction opposite to the side of the opening) from a level of the inner bottom 41e2 of the cylindrical portion 41a and is formed into a doughnut shape having a predetermined width on an underside. As shown in FIG. 7, there is a difference of elevation D between the outer bottom 41e1 and inner bottom 41e2. Further, an approximately hemispherical retention unit 41e3 is provided in the central part of the inner bottom 41e2 and bulging from the level of the inner bottom 41e2 toward the level of the outer bottom 41e1. The retention unit 41e3 is used to retain the dome-shaped rear end of the trunk cover 11b of the capsule-type medical device 2 and has a cross-shaped projection 41e4 which is provided inside and projecting toward the opening so that the entire rear end is uniformly sterilized when a sterilizing gas enters toward the rear end, which is retained in a line-contact manner, of the trunk cover 11b. The projection 41e4 may be formed as a plurality of projections, each of which retains the rear end of the capsule-type medical device 2 by point contact.

The handle portion 41b is formed of a tabular member whose upper surface is approximately triangular and configured, as shown in FIG. 5, so that a handle portion 42b of the inner lid unit 42 described later can come into contact therewith. The edge portion 41c has a predetermined width and is provided like a stair around the upper hem of the opening of the cylindrical portion 41a and around the outer circumference of the handle portion 41b one step higher than the upper hem and the handle portion 41b so as to restrain movement of a handle portion, which is in contact with the handle portion 41b, of the inner lid unit 42. Further, the edge portion 41c is constructed to have a height equal to or more than a thickness of the handle portion 42b, which is in contact with the handle portion 41b, or an edge portion 42c of the inner lid unit 42 so that the sterilized sheet 43 can be attached to the upper surface of the edge portion 41c while the inner lid unit 42 is contained inside the blister pack 41.

The projection 41d is formed of a substantially half-column-shaped projection arranged in a longitudinal direction of the cylindrical portion 41a and configured to have the largest diameter at its upper end (opening side of the cylindrical portion 41a) with the diameter gradually decreasing toward the lower end (bottom 41e side). Plural projections, each having an identical shape, are arranged approximately at regular intervals around the cylindrical portion 41a along the longitudinal direction thereof. The projection 41d has an opening at its upper end and a semi-dome-shaped bottom formed at its lower end. In the first embodiment, five projections 41d are arranged approximately at regular intervals on a circumferential surface of the cylindrical portion 41a.

The inner lid unit 42 includes, as shown in FIGS. 8 and 9, a bottomed cylindrical portion 42a, a tongue-shaped handle portion 42b provided in a portion of the upper hem of the opening of the cylindrical portion 42a, an edge portion 42c provided around the upper hem of the opening of the cylindrical portion 42a and connects to the handle portion 42b, and a plurality of substantially half-column-shaped projections 42d bulging in the outward direction from the cylindrical portion 42a.

The cylindrical portion 42a has, as shown in FIGS. 8 to 12, a bottom 42e and a protrusion unit 42e1 having a hole for retaining the capsule-type medical device 2 is provided in the central part of the bottom 42e. The protrusion unit 42e1 is formed in a substantially cylindrical shape which appears to be an upward projection when viewed in vertical section, and an upper surface thereof bulges inside the cylindrical portion 42a (towards the opening direction) from the level of the bottom 42e. An inside diameter of the protrusion unit 42e1 is slightly larger than the outside diameter of the capsule-type medical device 2. A plurality of projections 42e2 in a straight shape, four in the present embodiment, are formed on the inner circumference of the protrusion unit 42e1 in the longitudinal direction toward the opening of the protrusion unit 42e1. Further, a step portion 42e3 is provided near an upper surface side of the protrusion unit 42e1 and the inside diameter of the step portion 42e3 is configured to be smaller than that of the protrusion unit 42e1 on the opening side. When the inner lid unit 42 is contained inside the blister pack 41, as shown in FIG. 12, the bottom 42e including the protrusion unit 42e1 of the cylindrical portion 42a and the inner bottom 41e2 including the retention unit 41e3 of the blister pack 41 form a retention space area 40a to make it possible to contain and retain the capsule-type medical device 2.

In the first embodiment, when the distal-end cover 11a of the capsule-type medical device 2 is inserted into the protrusion unit 42e1, as shown in FIGS. 9 and 12, the projections 42e2 retain a portion of the trunk cover 11b of the hermetic container 11 by line contact and also a tip part of the step portion 42e3 retains a portion of the distal-end cover 11a by line contact so that a mirror finish unit 11a1 in the range of the dashed dotted line a-a is not in contact with component parts of the protrusion unit 42e1 including the projections 42e2 and step portion 42e3. The projections 42e2 are not necessarily formed along the longitudinal direction of the protrusion unit 42e1 in a straight shape, and may be structured, for example, as plural projections that are formed on the protrusion unit 42e1 so as to each retain a portion of the trunk cover 11b of the hermetic container 11 by point contact.

The handle portion 42b is an approximately triangular tabular member whose upper surface is substantially smaller than that of the handle portion 41b and is formed, as shown in FIGS. 8 and 11, integrally with the edge portion 42c provided around the upper hem of the opening of the cylindrical portion 41a. The handle portion 42b is structured so that the handle portion 42b can come into contact with the handle portion 41b of the blister pack 41 when the inner lid unit 42 is contained inside the blister pack 41. The edge portion 42c is provided around the upper hem of the opening of the cylindrical portion 42a and structured so that the edge portion 42c can come into contact with the upper hem of the opening of the blister pack 41 when the inner lid unit 42 is contained inside the blister pack 41. The thickness of the handle portion 42b and edge portion 42c, as described above, is set to be equal to or less than that of the edge portion 41c of the blister pack 41. Therefore, when the inner lid unit 42 is contained inside the blister pack 41, movement of the handle portion 42b is restricted to a range set by the width of the handle portion 41b because of the edge portion 41c, and when the sterilized sheet 43 is attached to the upper surface of the edge portion 41c, the entire inner lid unit 42 including the handle portion 42b and edge portion 42c is contained inside the blister pack 41.

The projection 42d is an approximately half-column-shaped projection provided in the longitudinal direction of the cylindrical portion 42a, each of which is arranged approximately at regular intervals around the cylindrical portion 42a along the longitudinal direction thereof. The projection 42d has an opening at its upper end and a semi-dome-shaped bottom formed at its lower end. In the first embodiment, five projections 42d are arranged approximately at regular intervals on the circumferential surface of the cylindrical portion 42a. The projections 42d are formed in such a manner that a tip of each projection 42d can contact an inner circumferential surface of the cylindrical portion 41a at a position not opposing to the projection 41d of the blister pack 41 when the inner lid unit 42 is contained inside the blister pack 41 and the handle portions 41b and 42b are in contact, whereby the projections 42d prevent wobbling of the inner lid unit 42 inside the blister pack 41.

A passage 40b is formed of a gap between the inner circumferential surface of the projection 41d of the blister pack 41 and outer circumferential surface of the cylindrical portion 42a of the inner lid unit 42, as shown in FIGS. 5, 11, and 12, to allow for a passage of a sterilizing gas that enters from outside via the sterilized sheet 43. The passage 40b and the retention space area 40a are communicated with each other so as to allow a sterilizing gas that has passed passage 40b to reach the retention space area 40a.

Figure 13:
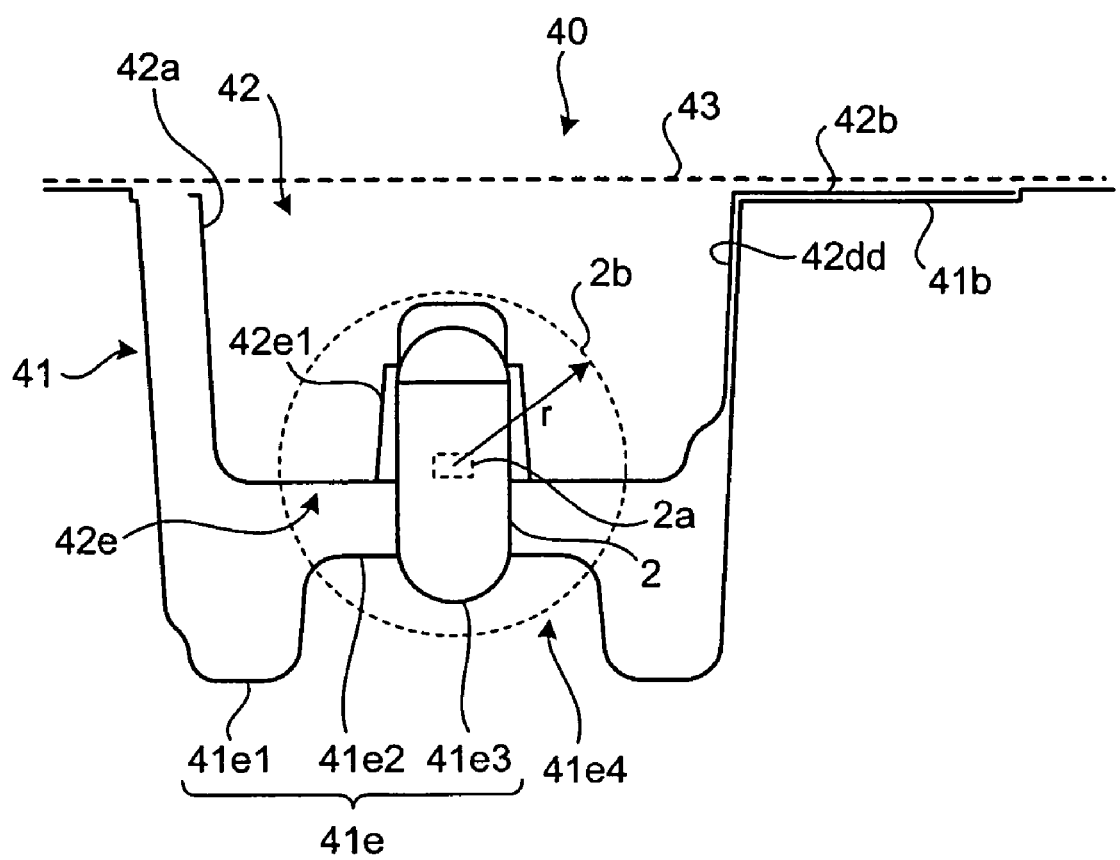
FIG. 13 is a B-B line sectional view of the container case for describing a range in which power supply is operable.

Further, as shown in FIG. 13, the capsule-type medical device 2 has a reed switch 2a for power supply inside to perform an on/off operation in accordance with a magnetic field from outside. When the reed switch 2a is turned into an on-state to allow for the power supply to each function executing unit, the LED 20 shown in FIG. 2 blinks to notify such state to the outside. The reed switch 2a is provided in an approximately central part in the longitudinal direction of the capsule-type medical device 2 and has a spherical power supply operable range 2b of a radius r around the reed switch 2a. When a permanent magnet (not shown) approaches the power supply operable range 2b and a predetermined magnetic force is applied, the reed switch 2a is turned on and becomes capable of performing a power supply operation. In the first embodiment, the diameter of the bottom 41e of the blister pack 41 and that of the bottom 42e of the inner lid unit 42, for example, are set to be longer than the diameter 2r of the power supply operable range 2b. Further, the power supply operable range 2b in the first embodiment is set to such a range that, when the capsule-type medical device 2 is retained by the retention unit 41e3 of the blister pack 41 and protrusion unit 42e1 of the inner lid unit 42, the power supply operable range 2b covers the inner bottom 41e2, the retention unit 41e3, and the protrusion 42e1, extends to a level between the level of the outer bottom 41e1 and the level of the inner bottom 41e2, and does not extend over the height of the cylindrical portion 42a.

When the capsule-type medical device 2 is to be used, the sterilized sheet 43 is peeled off from the container case 40, a magnetic body is put inside the cylindrical portion 42a of the inner lid unit 42, and the reed switch is turned into the on-state due to a magnetic field of the magnetic body placed inside. Then, blinking of the LEDs 20 can be confirmed through the transparent or semitransparent protrusion unit 42e1. Thus, the protrusion unit 42e1 has, in addition to functions to retain and protect the capsule-type medical device 2, a function to facilitate confirmation of blinking of LEDs.

As the magnetic body, a permanent magnet such as a ferrite magnet and neodymium magnet may be used, or any other magnetized metal body or an electromagnet if a desired magnetic field is generated.

Figure 14:
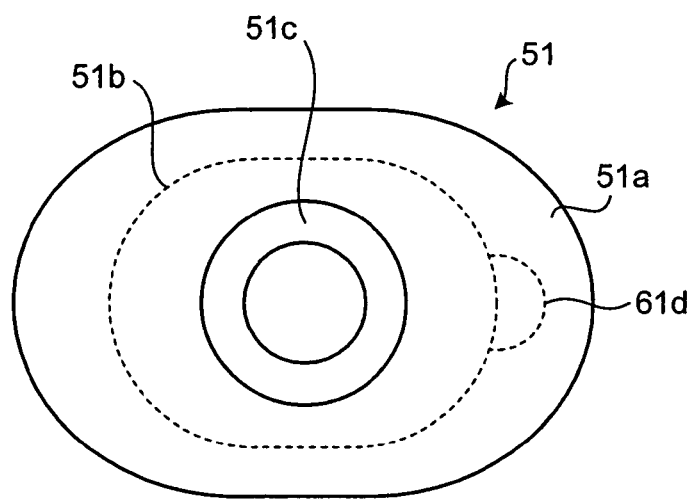
FIG. 14 is a plan view of the power-supply starter for a capsule-type medical device.
Figure 15:
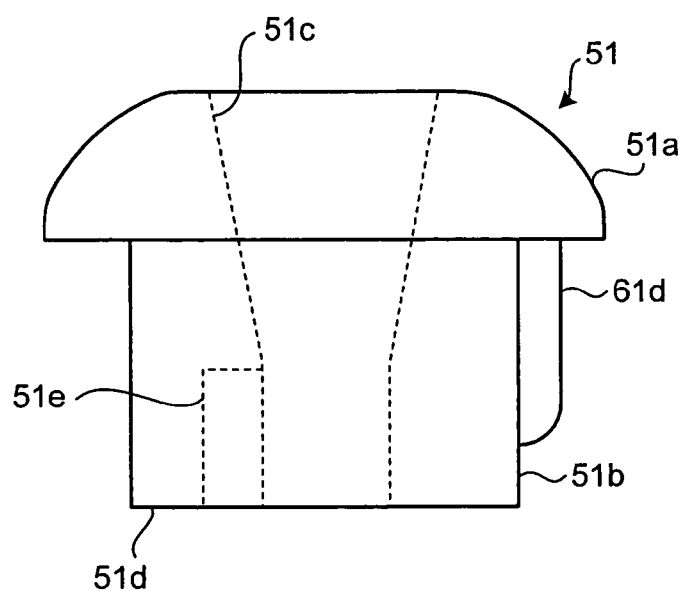
FIG. 15 is a side view of the power-supply starter for the capsule-type medical device.

In the first embodiment, when using the capsule-type medical device 2, a power-supply starter for a capsule-type medical device (hereinafter referred to simply as a "power-supply starter") 51 shown in FIGS. 14 and 15 is used to change the reed switch 2a from an off state to an on state to switch to a power supply state.

The power-supply starter 51 includes a handle portion 51a provided in an upper part thereof and a cylindrical portion 51b in a cylindrical shape provided in a lower part thereof, and the handle portion 51a and the cylindrical portion 51b are integrally formed. Further, a hole 51c is provided along the longitudinal direction of the cylindrical portion 51b so as to penetrate through the central part of the handle portion 51a.

Further, the cylindrical portion 51b has a projection 61d, which is characteristic of the first embodiment, provided on its flank, and the projection 61d is engaged with one of five guide grooves 42dd, which are recesses of the five projections 42d provided on the circumferential surface of the cylindrical portion 42a, thereby restricting the movement of the power-supply starter 51 only to an insertion/removal direction A. In other words, the power-supply starter 51 is prevented from rotating around an axis of the capsule-type medical device 2.

Figure 16:
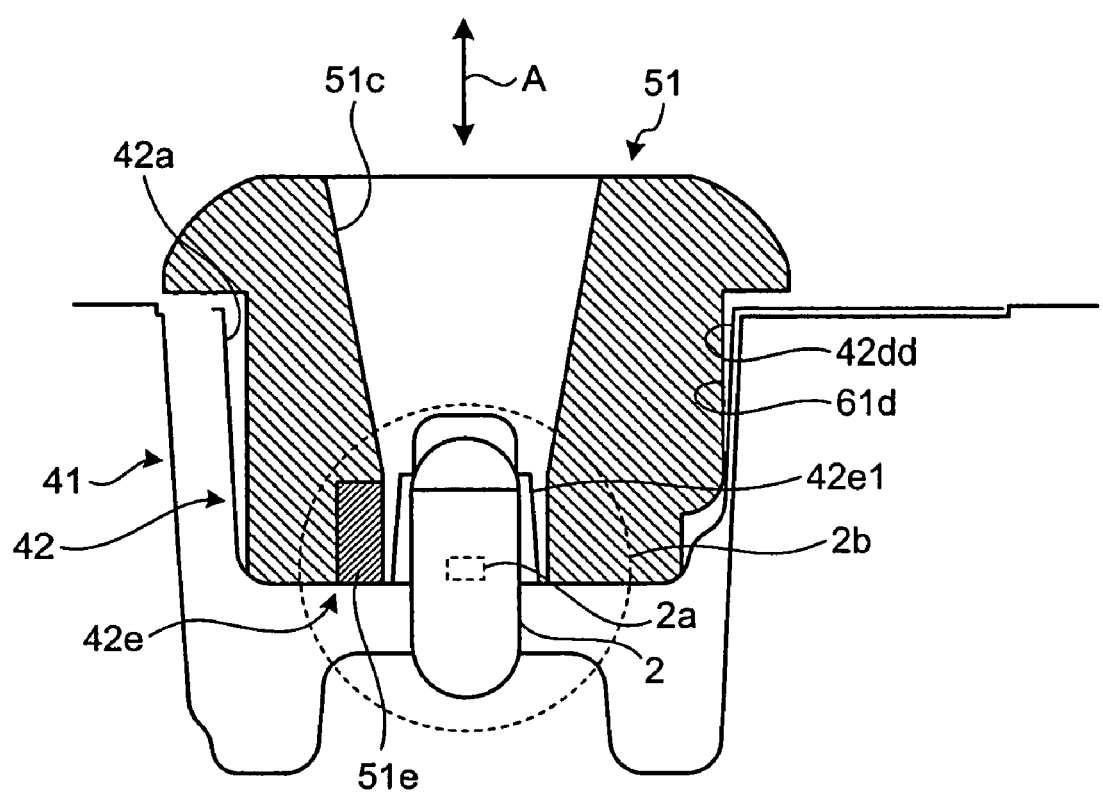
FIG. 16 is a sectional view showing a power-supply starter apparatus for a capsule-type medical device when the power-supply starter for a capsule-type medical device is fitted into the container case.

The handle portion 51a is formed, as shown in FIGS. 14 and 15, into an approximately elliptic shape on its upper surface and an approximately trapezoidal shape on its side. The cylindrical portion 51b has a magnetic body 51e provided on an inner wall side of a bottom 51d. FIG. 16 is a B-B cross sectional view of FIG. 11 after the power-supply starter 51 is fitted. In FIG. 16, the diameter at the bottom 51d of the hole 51c is formed a little larger than that of the protrusion unit 42e1 of the inner lid unit 42 and the hole 51c is formed in a tapered form with an increasing diameter upwards from halfway through the hole 51c. Further, the hole 51c is formed longer than the protrusion unit 42e1 of the inner lid unit 42. Thus, if the sterilized sheet 43 is peeled from the container case 40, the power-supply starter 51 can be engaged with the protrusion unit 42e1 like wrapping the entire protrusion unit 42e1 from the upper surface side of the inner lid unit 42. The diameter of the hole 51c is made to increase upwards in a tapered form so as to facilitate confirmation when the LEDs 20 of the capsule-type medical device 2 are blinking. Conversely, it is also possible to structure the hole 51c in a tapered form with a decreasing diameter upwards and form the power-supply starter 51 in, for example, a blackish color so that an operator can recognize blinking of the LEDs 20 easily through the opening of the hole 51c.

The outside diameter (diameter) of the cylindrical portion 51b is made smaller, for example, than the diameter 2r of the power supply operable range 2b of the reed switch 2a, and the magnetic body 51e provided inside the cylindrical portion 51b is formed of a square-shaped magnet of a predetermined-size curved like, for example, the inner wall of the cylindrical portion 51b. When the power-supply starter 51 is engaged with the protrusion unit 42e1 of the inner lid unit 42 as if to wrap around the protrusion unit 42e1; the magnetic body 51e comes within the power supply operable range 2b and the reed switch 2a is turned on by a magnetic field of the magnetic body 51e thereby switching to the power supply state. Then, a blinking state of the LEDs 20 can be confirmed through the hole 51c.

Figure 17:
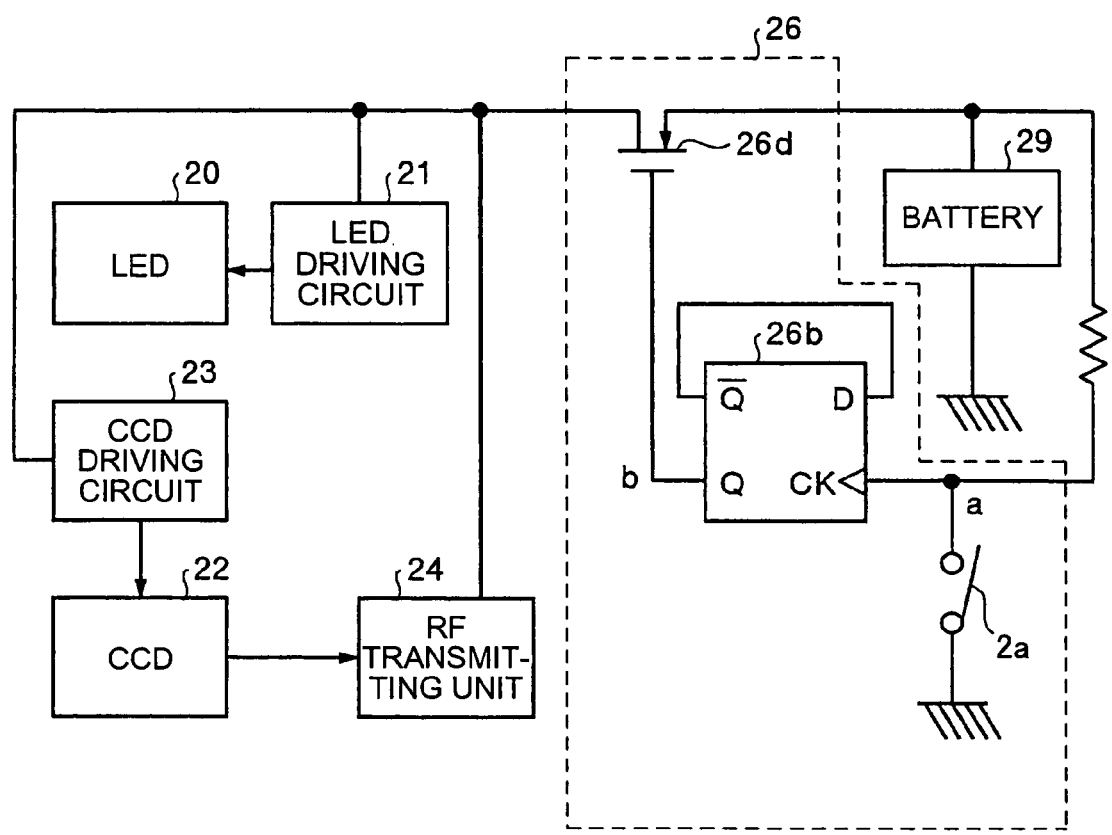
FIG. 17 is a circuit diagram showing a circuit configuration of a system control circuit of the capsule-type medical device shown in FIG. 3.

Here, a circuit configuration of the system control circuit 26 of the capsule-type medical device 2 shown in FIG. 3 will be described based on a circuit diagram shown in FIG. 17. In FIG. 17, the system control circuit 26 includes the reed switch 2a which has a grounded first end and a second end connected to a latch circuit, a flip-flop 26b constituting the latch circuit, and an FET 26d connected to the flip-flop 26b to function as a power switching device. The reed switch 2a performs an on/off operation in accordance with a magnetic field applied from outside and, when a clock corresponding to the on/off operation of the reed switch 2a is input, the flip-flop 26b turns the FET 26d to the on state.

That is, when a magnetic field is applied from outside, the reed switch 2a is switched to the on state and point "a" in the diagram changes from a high (H) level to a low (L) level. When the magnetic field is no longer applied, the reed switch 2a is switched to the off state and point "a" changes from the L level to the H level. According to the on/off operation described above, a clock corresponding to the on/off operation is input into a CK terminal of the flip-flop 26b. The flip-flop 26b outputs from Q a signal (signal at a point "b") obtained through frequency division of a signal at the point "a" at a rising edge from the L level to the H level. When the Q output of the flip-flop 26b is at the L level, the FET 26d is turned to the on state so as to allow for the power supply from the battery 29 to the LED driving circuit 21 and the CCD driving circuit 23 thereby activating the LED driving circuit 21 and the CCD driving circuit 23, whereby the driving of the LEDs 20, the CCD 22, and the RF transmitting unit 24 becomes possible and the LEDs 20 are lit.

Next, when a magnetic field is applied from outside, a signal on the point "a" changes from the H level to the L level again. The operation causes the Q output of the flip-flop 26b to attain the H level (signal at the point "b") and the FET 26d is turned to the off state to stop the power supply to the entire circuit, so that the LEDs 20 are put out. Next, when a magnetic field is applied again from outside, a signal on the point "a" changes from the H level to the L level again. The operation causes the Q output of the flip-flop 26b to attain the L level (signal at the point "b") and the FET 26d is turned to the on state to supply power from the battery 29 to the LED driving circuit 21, the CCD driving circuit 23, and the RF transmitting unit 24 so that the LEDs 20 are lit. When a magnetic field is applied to the reed switch 2a, as described above, the FET 26d is switched on and off according to a so-called toggle operation. Specifically, the FET 26d performs a toggle operation, in which the state of the FET 26d is switched from off to on or on to off, each time the power-supply starter 51 is inserted or removed.

Therefore, the LEDs 20 may be set in a distinguished state according to the toggle operation described above at a time of shipment of the capsule-type medical device 2 from a factory, whereas the capsule-type medical device 2 may be turned into a power-supply state according to the toggle operation caused by an insertion/removal of the power-supply starter 51 when used for the subject, for example.

Figure 18:
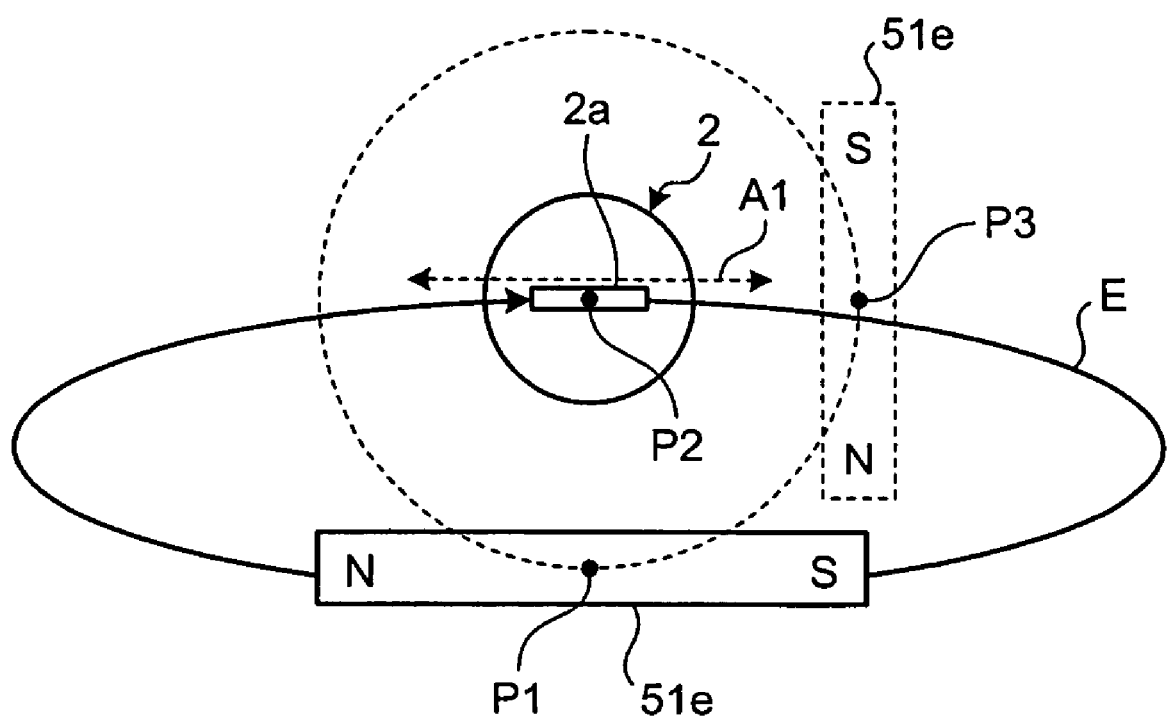
FIG. 18 is a schematic diagram showing a relationship between a magnetic field generated by a magnetic body and a reed switch inside the capsule-type medical device shown in FIG. 16.

The reed switch 2a can only detects a magnetic force applied in the longitudinal direction and not a magnetic force in a direction perpendicular to the longitudinal direction. Thus, in order to realize the toggle operation described above, there must be an arrangement in which a magnetic field E formed by the magnetic body 51e can be applied from the longitudinal direction A1 of the reed switch 2a, as shown in FIG. 18. If the magnetic body 51e located at a position P1 is moved (rotated) to a position P3 by rotating around a position P2 of the reed switch 2a by 90°, the reed switch 2a cannot detect magnetism and therefore cannot switch to the on state.

Thus, when the power-supply starter 51 is rotated in the circumferential direction of the capsule-type medical device 2 by up to 90° while the capsule-type medical device 2 is retained by the protrusion unit 42e1, the reed switch 2a always crosses the magnetic field E and a magnetic force of the magnetic body 51e reaches the reed switch 2a to turn on the reed switch 2a so that the LEDs 20 can be lit. However, if the power-supply starter 51 is further rotated, the toggle operation is repeated and the FET 26 is repeatedly set to the on/off states. Therefore, if the capsule-type medical device 2 is allowed to rotate freely around the axis, it becomes difficult to set the on state or the off state securely.

In the first embodiment, the capsule-type medical device 2 is not allowed to rotate around the axis, and the toggle operation is performed solely depending on the insertion/removal of the power-supply starter 51 in the longitudinal direction of the capsule-type medical device 2, whereby the on state and off state can reliably be set.

Figure 19:
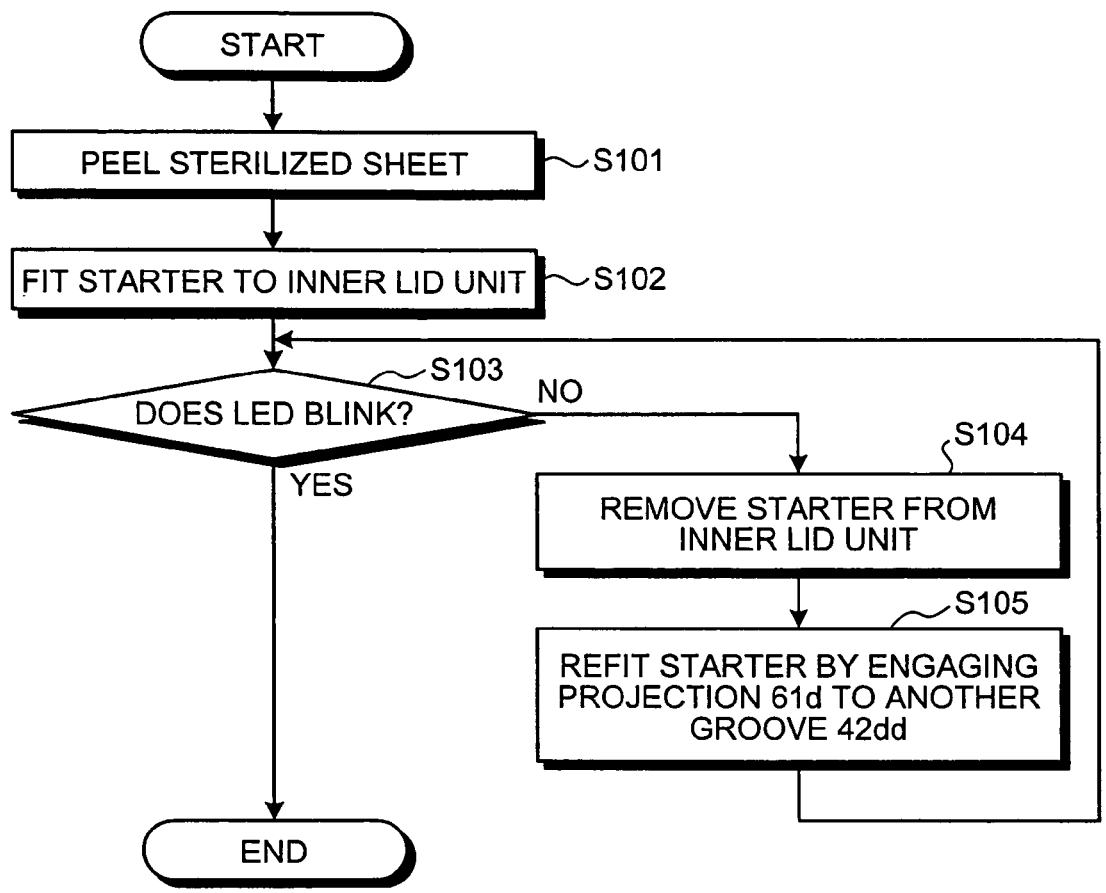
FIG. 19 is a flow chart showing a procedure for starting a power supply operation of the capsule-type medical device shown in FIG. 17.

Here, switching processing of the power supply state of the capsule-type medical device 2 will be described with reference to the flow chart shown in FIG. 19. In FIG. 19, when the capsule-type medical device 2 is to be used, the sterilized sheet 43 is first peeled from the container case 40 in a sterilized state, as shown in FIG. 5 (step S101). Thereafter, the power-supply starter 51 is inserted into the inner lid unit 42 from an insertion/removal direction A to fit to the protrusion unit 42e1 while the projection 61d of the power-supply starter 51 is engaged with the groove 42dd (step S102).

Then, whether the LEDs 20 blink or not is determined (step S103) and if the LEDs 20 do not blink (step S103, No), the power-supply starter 51 is removed from the inner lid unit 42 (step S104), then the power-supply starter 51 is refitted to the inner lid unit 42 from the insertion/removal direction while the projection 61d is made to be engaged with one of the other grooves 42dd (step S105), and whether the LEDs 20 blink or not is determined again.

If the LEDs 20 blinks (step S103, Yes), the present processing is finished.

In a power-supply starter apparatus for a capsule-type medical device according to the first embodiment, since the insertion/removal of the power-supply starter 51 causes the toggle operation of the power-supply switching, a power supply stop operation can also be performed to cause a transition from a power-on state to a power-of state. When the power supply stop operation is performed, the determination of step S103 is replaced by determination on whether LEDs 20 have been put out or not, and the steps S102 to S105 will be repeated.

Figure 20:
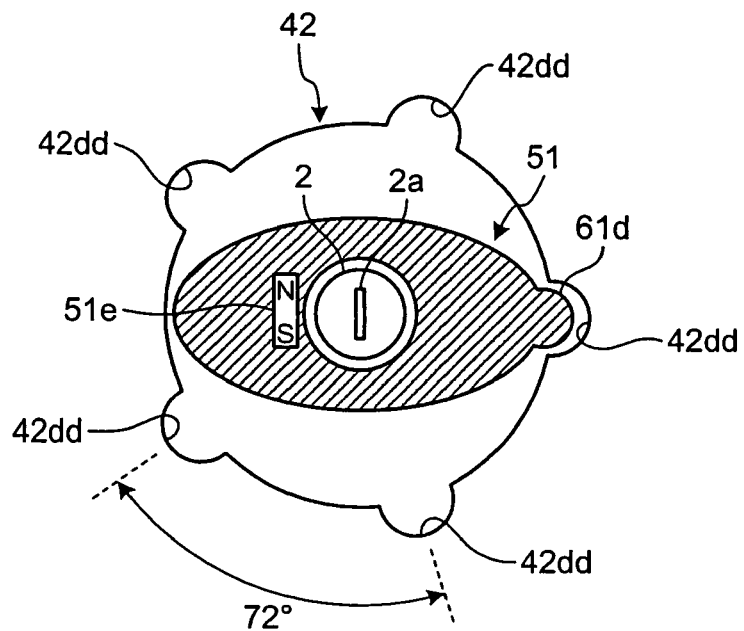
FIG. 20 is a sectional view showing the configuration of a power-supply starter apparatus for a capsule-type medical device in a first embodiment of the present invention.

FIG. 20 is a horizontal cross sectional view showing an engagement (fitting) state of the inner lid unit 42 and the power-supply starter 51 in a power-supply starter apparatus for a capsule-type medical device in the first embodiment. In FIG. 20, a relationship between the reed switch 2a and the magnetic body 51e shown in FIG. 18 is met and the toggle operation is performed by inserting/removing the power-supply starter 51 in this engagement state.

Here, since five grooves 42dd are arranged at regular intervals, that is, equiangularly at a central angle of 72° on the inner circumference of the inner lid unit 42 in FIG. 20, even if the power supply state is not switched by the first insertion/removal of the power-supply starter 51, the power supply state will always be switched by inserting/removing the power-supply starter 51 by engaging with one of the other grooves 42dd.

If the central angle between adjacent grooves 42dd is less than 90°, the power supply state is always switched by an insertion/removal operation in which one of the grooves 42dd is engaged. If five or more grooves 42dd with an equal central angle between grooves 42dd are set, the power supply state is always switched by an insertion/removal operation in which one of the grooves 42dd is engaged. In the first embodiment, the positional relationship between the inner lid unit 42 and the reed switch 2a of the capsule-type medical device 2 is not fixed.

In the first embodiment, the movement of a power-supply starter is restricted to the insertion/removal direction of the power-supply starter and a capsule-type medical device is prevented from rotating around the axis, when the power-supply starter having a magnetic body is fitted to an inner lid unit which retains a capsule-type medical device, and a magnetic field of the magnetic body is applied to the capsule-type medical device from outside of the inner lid unit, whereby a power supply state can be switched reliably only by an insertion/removal operation of the power-supply starter. Further, driving of each function of the capsule-type medical device can be started at any time, for example, immediately before using the capsule-type medical device for a subject, and driving of each function can be stopped at any time so that consumption of power stored in the capsule-type medical device can be suppressed.

First Modification of the First Embodiment

Figure 21:
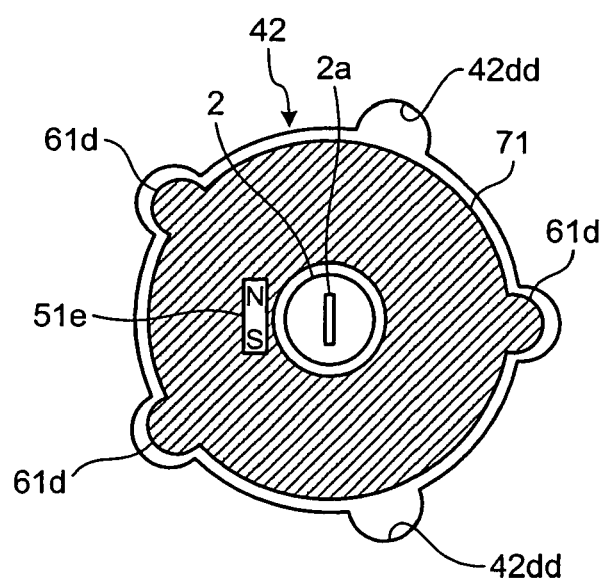
FIG. 21 is a sectional view showing the configuration of a power-supply starter apparatus for a capsule-type medical device in a first modification of the first embodiment of the present invention.
Figure 22:
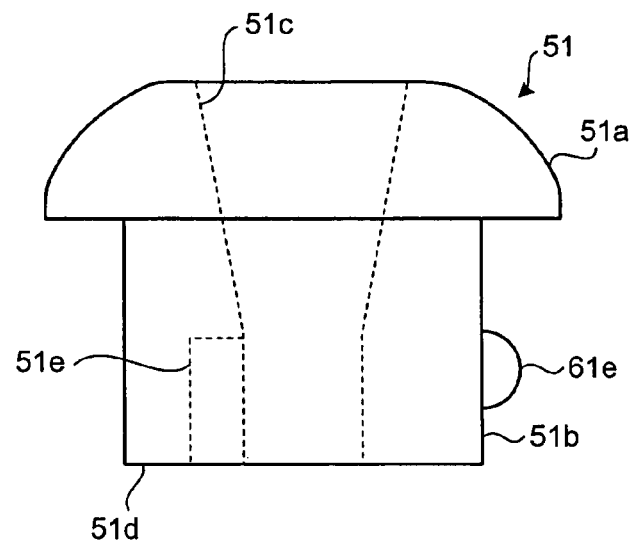
FIG. 22 is a sectional view showing the configuration of a power-supply starter apparatus for a capsule-type medical device in a second modification of the first embodiment of the present invention.

In a first modification of the first embodiment, the configuration of the inner lid unit 42 is the same as that in the first embodiment, but the configuration of the power-supply starter is different. As shown in FIG. 21, a power-supply starter 71 of the first modification of the first embodiment has an approximately circular cross section and the outer circumferential surface thereof approximately matches with the inner circumferential surface of the inner lid unit 42. Further, the power-supply starter 71 has three projections 61*d* formed corresponding to the five grooves 42*dd* provided on the inner circumferential surface of the inner lid unit 42.

Since the central angles formed by adjacent grooves 42*dd* are approximately the same, each of the three projections 61*d* is engaged with one of the five grooves 42*dd* and guided, so as to prevent the rotation of the capsule-type medical device 2 around the axis while allowing the movement only in the insertion/removal direction.

Second Modification of the First Embodiment

In the first modification of the first embodiment described above, all projections 61*d* have a shape fitting to the groove 42*dd*, but in a second modification, the projection 61*d* is replaced with a projection 61*e* which is formed only by a tip side portion in the insertion direction of the projection 61*d*.

Since the projection 61*e* is also engaged with the groove 42*dd* and guided when the capsule-type medical device 2 is inserted/removed in the second modification, the movement of the capsule-type medical device 2 is restricted only to the insertion/removal direction.

Third Modification of the First Embodiment

Figure 23:
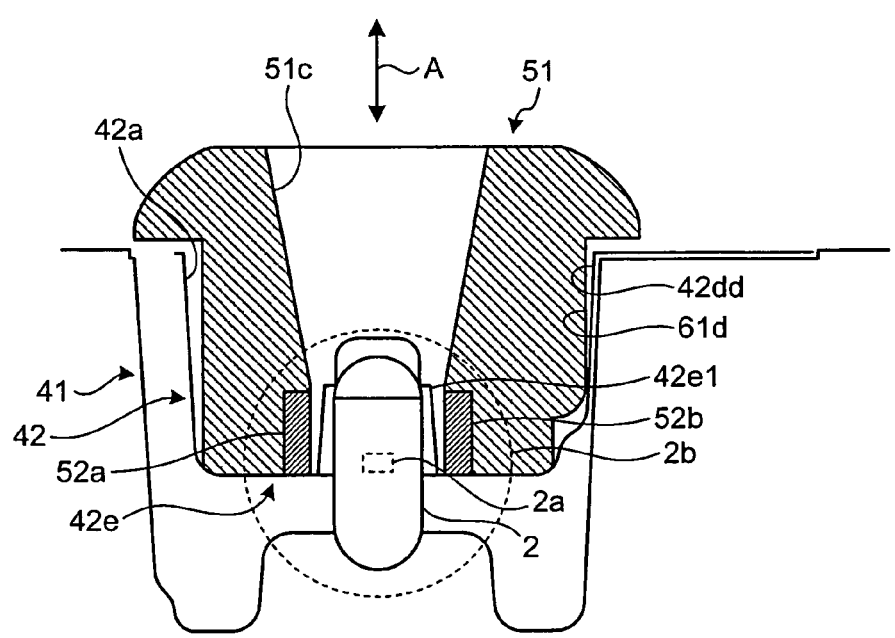
FIG. 23 is a sectional view showing the configuration of a power-supply starter apparatus for a capsule-type medical device in a third modification of the first embodiment of the present invention.

In a third modification, as shown in FIG. 23, a plurality of magnetic bodies 52*a* and 52*b* are arranged at positions facing the cylindrical portion 51*b* of the power-supply starter 51. As these magnetic bodies 52*a* and 52*b*, magnetic bodies whose thickness is thinner than that of the magnetic body 51*e* and whose magnetic force is weak, for example, approximately half that of the magnetic body 51*e* are used.

Since, in the third modification, a plurality of magnetic bodies are arranged at positions facing the cylindrical portion of the power-supply starter and the direction of the reed switch and that of a magnetic field applied to the reed switch are set to be equal, the same advantages as those of the first embodiment are obtained, and also the overall size of the power-supply starter can be made smaller because smaller magnetic bodies than that used for the power-supply starter in the first embodiment can be used.

Fourth Modification of the First Embodiment

Figure 24:
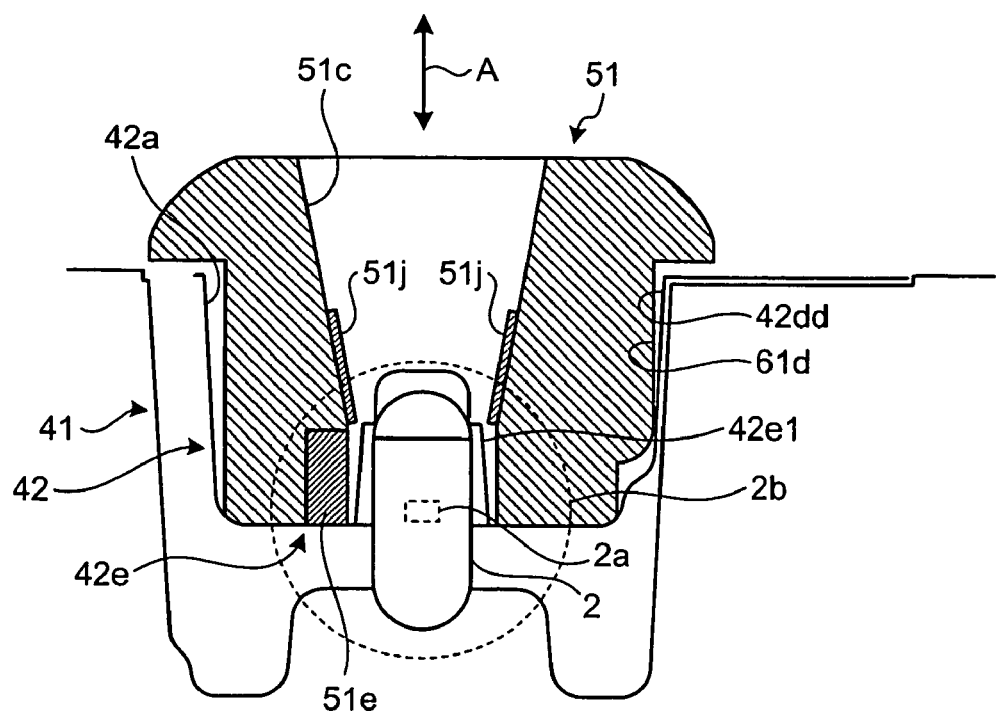
FIG. 24 is a sectional view showing the configuration of a power-supply starter apparatus for a capsule-type medical device in a fourth modification of the first embodiment of the present invention.

A fourth modification is configured, as shown in FIG. 24, to have, in addition to the hole 51*c*, reflectors 51*j* provided in a taper portion of the hole 51*c* of the power-supply starter 51 so that light from the lighted LEDs is reflected upwards in the hole 51*c*. In the modification, surface treatment, for example, may be given to the taper portion in the hole 51*c* so that the formed taper portion can reflect the light like a reflector.

Since the fourth modification is configured with the reflectors in the hole to reflect the light of the LED upwards, the operator can easily confirm the lighting of the LED by viewing, whereby visibility of LED lighting can be improved for confirmation.

Second Embodiment

In the first embodiment and modifications thereof described above, a plurality of positional relationships between an inner lid unit and power-supply starter are set when inserting/removing the power-supply starter. In the first embodiment shown in FIG. 20, for example, five positional relationships are possible and one of the five positional relationships is used for insertion/removal. In contrast, in a second embodiment, the rotational positional relationship between the inner lid unit and power-supply starter is fixed when inserting/removing the power-supply starter.

Figure 25:
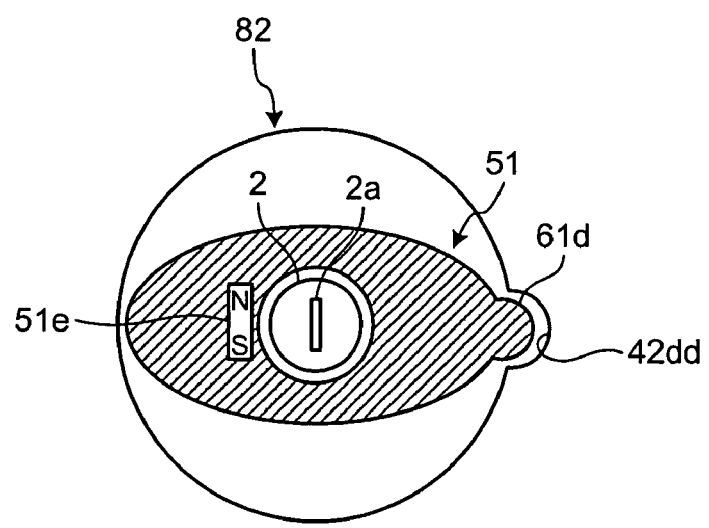
FIG. 25 is a sectional view showing the configuration of a power-supply starter apparatus for a capsule-type medical device in a second embodiment of the present invention.

Though the configuration of the power-supply starter 51 is the same as that in the first embodiment, as shown in FIG. 25, an inner lid unit 82 has a configuration obtained by eliminating four of the five grooves 42*dd* shown in the first embodiment. Other portions of the configuration are the same as those of the first embodiment. However, the projection 42*d* remains though the grooves 42*dd* are eliminated. That is, the grooves 42*dd* are filled to prevent them from functioning as a guide groove.

Thus, the power-supply starter 51 can be inserted/removed into/from the inner lid unit 82 only when one projection 61*d* engages with one groove 42*dd*.

The positional relationship between the inner lid unit 82 and the reed switch 2*a* of the capsule-type medical device 2 is fixed in advance and set so that the reed switch 2*a* is switched to the on state when the magnetic body 51*e* of the power-supply starter 51 is inserted.

Since, in the second embodiment, the power-supply starter is restricted to move only in the insertion/removal direction of the inner lid unit and prevented from rotating around the axis of the capsule-type medical device, and further the rotational positional relationship between the power-supply starter and inner lid unit is fixed, the power supply state can switched still more reliably.

First Modification of the Second Embodiment

Figure 26:
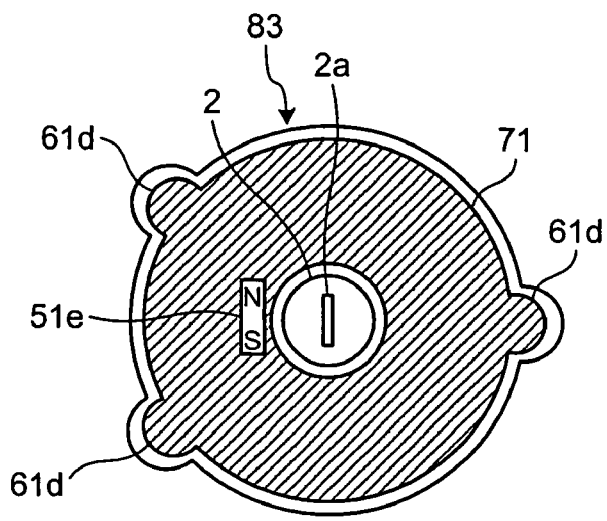
FIG. 26 is a sectional view showing the configuration of a power-supply starter apparatus for a capsule-type medical device in a first modification of the second embodiment of the present invention.

While one projection 61*d* and one groove 42*dd* are provided in the second embodiment described above, in a first modification of the second embodiment, three projections 61*d* and three grooves 42*dd* are provided as shown in FIG. 26 and each of the projections 61*d* corresponds to one of the grooves 42*dd*, so that three projections 61*d* fit into three grooves 42*dd*, respectively, only in one positional relationship. The configuration shown in FIG. 26 is obtained by eliminating two of the five grooves 42*dd* in the first modification of the first embodiment. The positional relationship between the power-supply starter 71 and an inner lid unit 83 is uniquely determined.

Second Modification of the Second Embodiment

Figure 27:
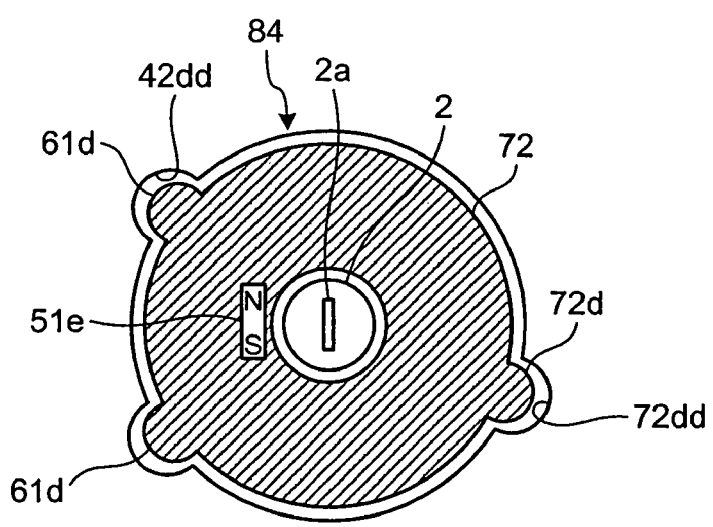
FIG. 27 is a sectional view showing the configuration of a power-supply starter apparatus for a capsule-type medical device in a second modification of the second embodiment of the present invention.

Though a second modification is similar to the first modification, arrangement of the plural projections 61*d* and the plural grooves 42*dd* is different from that in the first modification, so that circumferential distances between engaged units are different from each other as shown in FIG. 27. Such an arrangement also determines the positional relationship between the power-supply starter 72 and an inner lid unit 84 uniquely.

Third Embodiment

The rotational positional relationship between a power-supply starter and inner lid unit is uniquely determined by an engagement relationship between grooves and projections in the second embodiment described above, but in a third modification, the rotational positional relationship is uniquely determined by a cross sectional shape of an insertion portion of the power-supply starter and that of an insertion/removal space formed by the inner lid unit.

Figure 28:
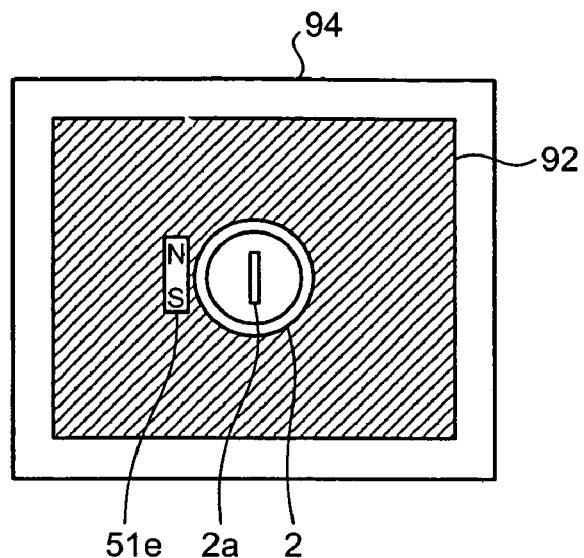
FIG. 28 is a sectional view showing the configuration of a power-supply starter apparatus for a capsule-type medical device in a third embodiment of the present invention.

In the third embodiment, as shown in FIG. 28, the cross sectional shape of the insertion/removal space formed by an inner lid unit 94 is rectangular and a power-supply starter 92 has a rectangular cross sectional shape internally touching the rectangle of the inner lid unit 94. In this case, the rotational, positional relationship is not uniquely determined, but a magnetic positional relationship between the magnetic body 51e and reed switch 2a is the same and thus the rotational positional relationship is substantially uniquely determined and the power-supply starter 92 is inserted/removed into/from the inner lid unit 94.

Since, also in the third embodiment, the power-supply starter is restricted to move only in the insertion/removal direction and prevented from rotating around the axis of the capsule-type medical device, the power supply state can reliably be switched by an insertion/removal operation of the power-supply starter.

First Modification of the Third Embodiment

Figure 29:
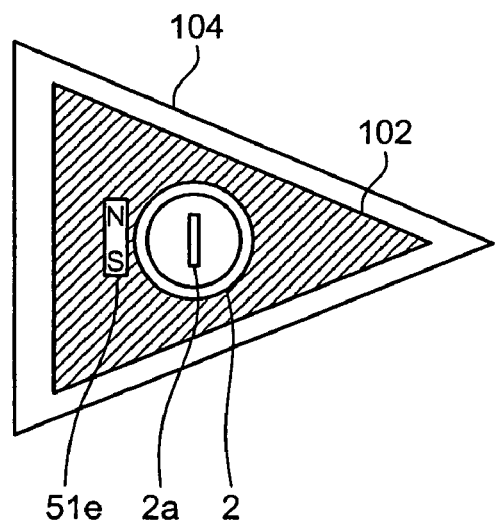
FIG. 29 is a sectional view showing the configuration of a power-supply starter apparatus for a capsule-type medical device in a first modification of the third embodiment of the present invention.

The cross sectional shape in the third embodiment described above is rectangular, but in a first modification, as shown in FIG. 29, the cross sectional shape is triangular. However, the cross sectional shape is not an equilateral triangle. This uniquely determines the rotational positional relationship between a power-supply starter 102 and an inner lid unit 104.

Second Modification of the Third Embodiment

Figure 30:
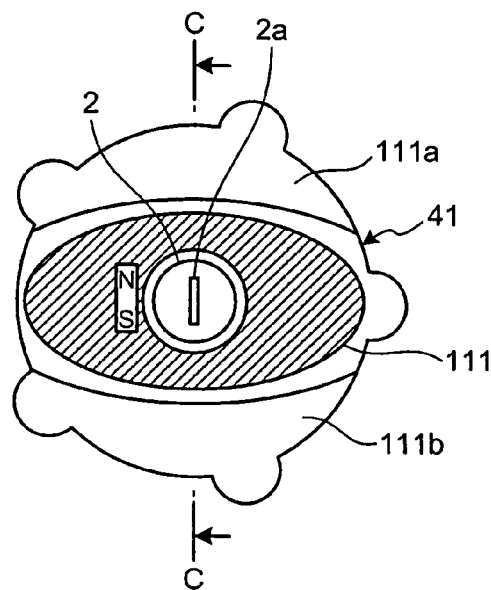
FIG. 30 is a sectional view showing the configuration of a power-supply starter apparatus for a capsule-type medical device in a second modification of the third embodiment of the present invention.
Figure 31:
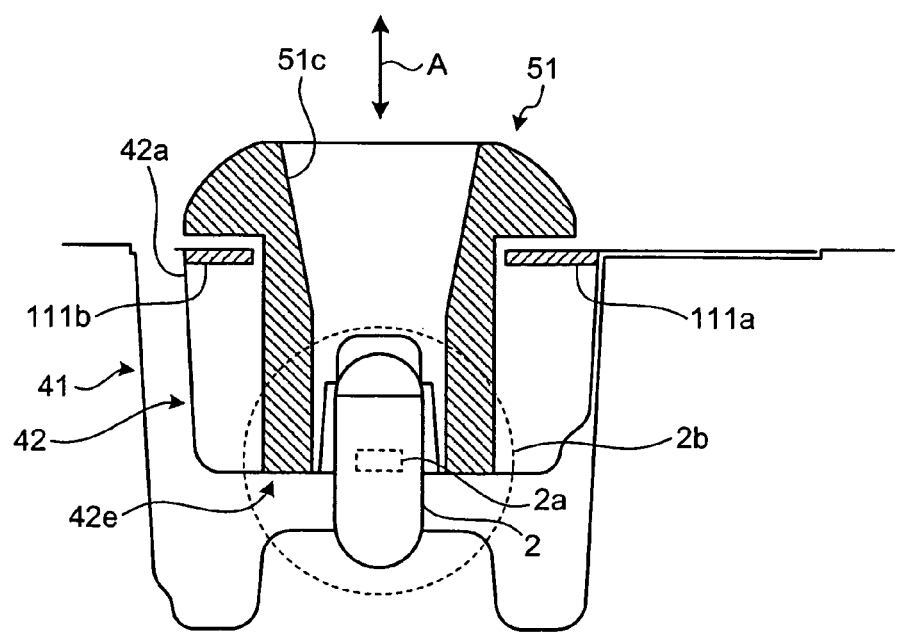
FIG. 31 is a C-C line sectional view of FIG. 30.

In a second modification, as shown in FIGS. 30 and 31, a power-supply starter 111 has a configuration obtained by eliminating the projection 61d from the power-supply starter 51 shown in the first embodiment and tabular cover units 111a and 111b externally touching the flanks of the power-supply starter 111 are provided on the upper surface of the inner lid unit so that the power-supply starter 111 can move only in the insertion/removal direction A without rotating. The second modification also determines the rotational positional relationship between the power-supply starter and inner lid unit uniquely.

The tabular cover units 111a and 111b are provided on the upper surface of the inner lid unit in the second modification, but as long as the magnetic body 51e is outside the power supply operable range 2b, the tabular cover units 111a and 111b may be provided lower than the position of the upper surface of the inner lid unit.

Further, in the first and second embodiments described above, the groove 42dd and the projection 61d may be in a loose engagement relationship. For example, the power-supply starter may have rotational fluctuations of about 10°. Still further, in the third embodiment, matching of cross sectional shapes need not be precise. What is essential is that the reed switch 2a is maintained in one of the on state and the off state and does not change the state even when the power-supply starter rotates.

Fourth Embodiment

It is assumed in each of the first to third embodiments described above that if a power-supply starter rotates while the power-supply starter is inserted in an inner lid unit, a toggle operation will be performed to switch a power supply state. In contrast, in a fourth embodiment, a reed switch is turned on/off only by insertion/removal of the power-supply starter by causing the reed switch and magnetic body to have a relationship so that the reed switch is not turned on/off even if the power-supply starter rotates while the power-supply starter is inserted.

Figure 32:
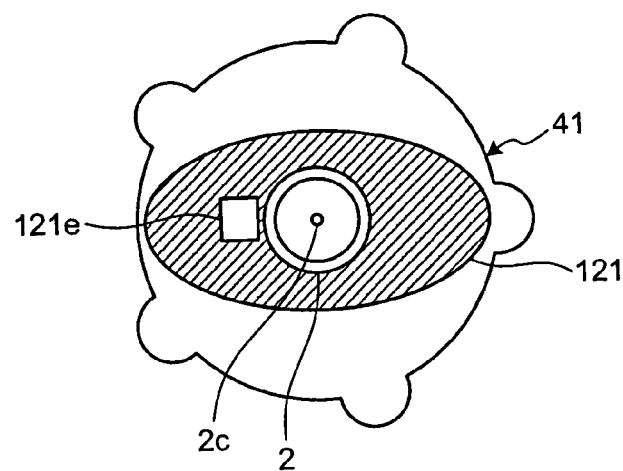
FIG. 32 is a sectional view showing the configuration of a power-supply starter apparatus for a capsule-type medical device in a fourth embodiment of the present invention.
Figure 33:
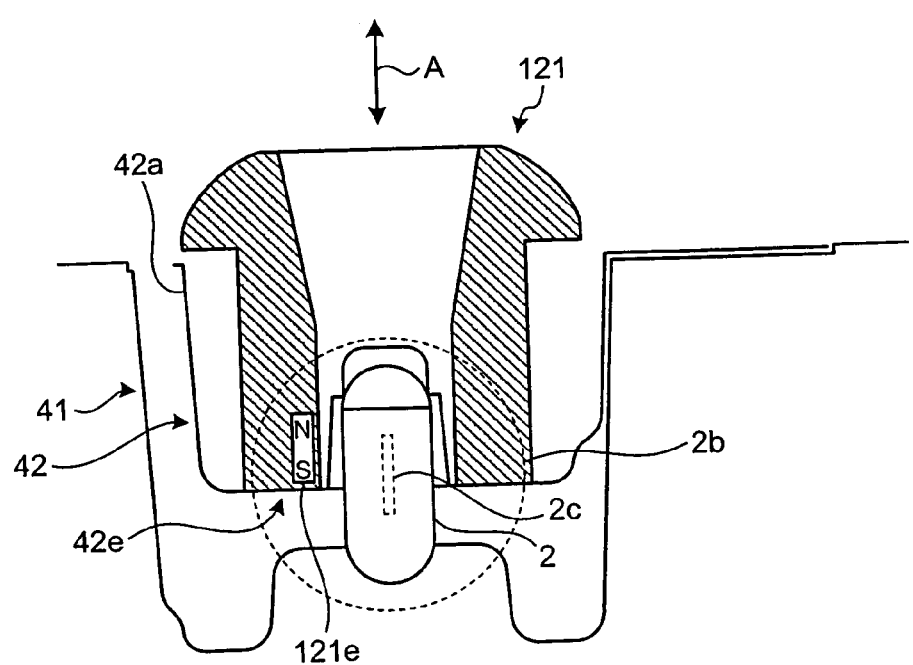
FIG. 33 is a longitudinal sectional view of FIG. 32.

As shown in FIGS. 32 and 33, the reed switch 2c is arranged so that the longitudinal direction of the reed switch 2c is along that of the capsule-type medical device 2. In contrast, a magnetic body 121e of a power-supply starter 121 is arranged facing the reed switch 2c so that an N-S direction of magnetic poles is along the longitudinal direction of the reed switch 2c.

Since a magnetic field applied to the reed switch 2c remains and changes little even if the power-supply starter 121, or the magnetic body 121e rotates around the axis of the capsule-type medical device 2, the power supply state is maintained. The power supply state is switched only by insertion/removal of the power-supply starter 121.

Since, in the fourth embodiment, the reed switch and the magnetic body are caused to have a arrangement relationship so that, even if the power-supply starter rotates, the on/off state of the reed switch is not changed and the power supply state is switched only in an insertion/removal direction of the power-supply starter, the power supply state can reliably be switched only by the insertion/removal operation of the power-supply starter.

Further advantages and modifications can easily be derived by a person skilled in the art. Thus, a wider range of aspects of the present invention is not limited to specific details disclosed and described above and representative embodiments. Therefore, various modifications can be made without deviating from the spirit or range of general concepts of the invention defined by attached claims or equivalents thereof.

Further, the above embodiments make reference to capsule-type medical devices acquiring mainly images, but the intra-subject information acquiring unit can be applied not only to the capsule-type medical devices that acquire images but also to capsule-type medical devices which acquire information about a living body such as pH and a temperature in the living body, and the same effects can be obtained.

What is claimed is:

1. A power-supply starter apparatus for a capsule-type medical device, comprising:
a container case internally retaining a capsule-type medical device having at least an intra-subject information acquiring unit and a power switch which switches power supply to each unit including the intra-subject information acquiring unit; and
a starter having a magnetic body to control switching of the power supply by applying a magnetic field generated by the magnetic body to the power switch of the capsule-type medical device inside the container case, wherein
the container case has an insertion/removal unit in which a space is formed where the magnetic body can be brought closer to the power switch and the starter is inserted/removed, and the insertion/removal unit and the starter have a restriction unit for restricting rotation of the starter around an axis in an insertion/removal direction into/from the insertion/removal unit so that switching of the power supply is controlled only by an insertion/removal operation of the starter.

2. The power-supply starter apparatus for the capsule-type medical device according to claim 1, further comprising a latch circuit for providing toggle switching output by frequency dividing a switching signal of the power switch, wherein the switching of power supply to each unit including the intra-subject information acquiring unit is controlled by the toggle switching output from the latch circuit.

3. The power-supply starter apparatus for the capsule-type medical device according to claim 1, wherein the restriction unit includes guide grooves provided in the insertion/removal unit for guiding the starter in the insertion/removal direction and projections provided on the starter to engage with the guide groove.

4. The power-supply starter apparatus for the capsule-type medical device according to claim 3, wherein the power switch is a reed switch and is arranged so that a direction perpendicular to an axis in a longitudinal direction of the capsule-type medical device is a longitudinal direction of the reed switch, the starter is inserted and removed in the longitudinal direction of the capsule-type medical device, the magnetic body is arranged so that a magnetic field is applied to the reed switch from the longitudinal direction of the reed switch, and the guide grooves are arranged at intervals of less than 90° around the axis in the insertion/removal direction.

5. The power-supply starter apparatus for the capsule-type medical device according to claim 4, wherein there are five or more guide grooves provided at equiangular intervals.

6. The power-supply starter apparatus for the capsule-type medical device according to claim 1, wherein the restriction unit restricts the rotation based on an inner cross sectional shape of the insertion/removal unit perpendicular to the insertion/removal direction and an outer cross sectional shape of the starter perpendicular to the insertion/removal direction.

7. The power-supply starter apparatus for the capsule-type medical device according to claim 1, wherein the restriction unit positions the insertion/removal unit and the starter in a rotational direction, and the capsule-type medical device is arranged inside the container case in advance so that a magnetic detection direction of the power switch of the capsule-type medical device and a direction of magnetism generated by the magnetic body of the starter match.

* * * * *